US 8,570,507 B1

(12) United States Patent
Cooper et al.

(10) Patent No.: US 8,570,507 B1
(45) Date of Patent: Oct. 29, 2013

(54) METHOD AND APPARATUS FOR ACQUIRING RAMAN SPECTRA WITHOUT BACKGROUND INTERFERENCES

(75) Inventors: John Cooper, Virginia Beach, VA (US); Mohamed F. Abdelkader, Norfolk, VA (US); Kent Wise, The Woodlands, TX (US)

(73) Assignee: Bruker Optics, Inc., Billerica, MA (US)

( * ) Notice: Subject to any disclaimer, the term of this patent is extended or adjusted under 35 U.S.C. 154(b) by 0 days.

(21) Appl. No.: 13/605,852

(22) Filed: Sep. 6, 2012

(51) Int. Cl.
*G01J 3/44* (2006.01)
(52) U.S. Cl.
USPC ........................................................ 356/301
(58) Field of Classification Search
USPC ................................................ 356/124, 301
See application file for complete search history.

(56) References Cited

U.S. PATENT DOCUMENTS

| | | | |
|---|---|---|---|
| 5,946,090 A | 8/1999 | Tashiro et al. | |
| 7,002,679 B2 | 2/2006 | Brady et al. | |
| 7,092,852 B1 | 8/2006 | Kane et al. | |
| 7,145,651 B2 | 12/2006 | Li et al. | |
| 7,177,022 B2 | 2/2007 | Wang et al. | |
| 7,864,311 B2 | 1/2011 | Klehr | |
| 2005/0068543 A1* | 3/2005 | Angeley | 356/521 |
| 2006/0120418 A1* | 6/2006 | Harter et al. | 372/30 |
| 2008/0030726 A1* | 2/2008 | Flanders et al. | 356/301 |

OTHER PUBLICATIONS

Hasegawa et al., "Separation of Raman spectra from fluorescence emission background by principal component analysis", Chemical Physics Letters 317, 6, 642, 2000.
Zhao et al., "Automated Autofluorescence Background Substraction Algorithm for Biomedical Raman Spectroscopy", Applied Spectroscopy, vol. 61, No. 11, 2007.
Zhao et al., "Integrated real-time Raman system for clinical in vivo skin analysis", Skin Research & Technology 14, 4, 2008.
Lieber et al., "Automated Method for Substraction of Fluorescence from Biological Raman Spectra", Applied Spectroscopy, vol. 57, Issue 11, pp. 1363-1367, 2003.
Mosier-Boss et al., "Fluorescence Rejection in Raman Spectroscopy by Shifted-Spectra, Edge Detection, and FFT Fittening Techniques", Applied Spectroscopy, vol. 49, Issue 5, pp. 630-638, 1995.
Zhang et al. "Enhanced Chemical Classification of Raman Images in the Presence of Strong Fluorescence Interference", Applied Spectroscopy, vol. 54, Issue 9, pp. 1379-1383, 2000.
Cormack et al., "Fluorescence suppression within Raman spectroscopy using annular beam excitation", Applied Physics Letters, vol. 91, Issue 2. 2007.
Schulmerich et al., "Dark Field Raman Microscopy", Analytical Chemistry, 82 (14) pp. 6273-6280, 2010.
Ru et al., "Direct Measurement of Resonance Raman Spectra and Cross Sections by a Polarization Difference Technique", Analytical Chemistry, 84, 11, 2012.
Benniston et al., "Detailed Picosecond Kerr-Gated Time-Resolved Raman Spectroscopy and Time-Resolved Emission Studies of Merocyanine 540 in Various Solvents", Journal of Physical Chemistry A, 107 (22) pp. 4347-4353, 2003.

(Continued)

*Primary Examiner* — Tarifur Chowdhury
*Assistant Examiner* — Abdullahi Nur

(57) ABSTRACT

One embodiment of a Raman spectrometer having a temperature controlled diode laser with Bragg grating optical feedback 100 which provides a means for the acquisition of Raman spectra using sequentially shifted excitations and provides a means for spectral processing to obtain a Raman spectrum which is free from background interference such as fluorescence.

25 Claims, 16 Drawing Sheets

(56) References Cited

OTHER PUBLICATIONS

Figure 1:
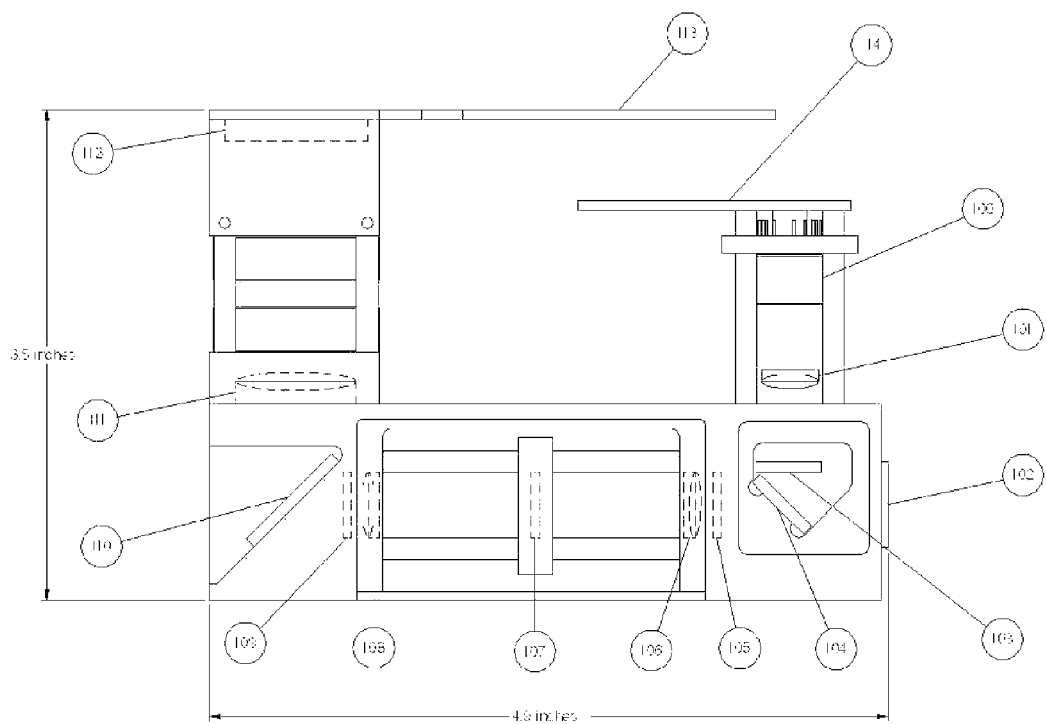

Efremov et al., "Fluorescence Rejection in Resonance Raman Speciroscopy Using a Picosecond-Gated Intensified Charge-Coupled Device Camera", Applied Spectroscopy, vol. 6, pp. 571-578, 2007.
Everall et al., "Picosecond Time-Resolved Raman Spectroscopy of Solids: Capabilities and Limitations for Fluorescence Rejection and the Influence of Diffuse Reflectance", Applied Spectroscopy, vol. 55, Issue 12, pp. 1701-1708, 2001.
Lakshmanna et al., "Ultrafast Raman loss spectroscopy: a new approach to vibrational structure determination", Current Science (00113891), 97, 2, 2009.
Mandal et al., "Temporal fluorescence rejection in Raman spectroscopy using femtosecond up-conversion with single- and multi-channel detection", Journal of Molecular Structure 735-736, 2005.
Martyshkin et al., "Effective suppression of fluorescence light in Raman measurements using ultrafast time gated charge coupled device camera", Review of Scientific Instruments, vol. 75, No. 3, 2004.
Matousek et al., "Fluorescence background suppression in Raman spectroscopy using combined Kerr gated and shifted excitation Raman difference techniques", Journal of Raman Spectroscopy 33, 238-242, 2002.
McCamant et al., "Femtosecond broadband stimulated Raman spectroscopy: Apparatus and methods", Review of Scientific Instruments, Vol. 75, No. 11, 2004.
Misra et al., "Pulsed remote Raman system for daytime measurements of mineral spectra", Spectrochimica Acta Part A: Molecular and Biomolecular Spectroscopy 61, 10, 2005.
Saariaho et al., "Resonance Raman Spectroscopy of highly fluorescing lignin containing chemical pulps:Suppression of fluorescence with an optical Kerr gate", International Journal of the Biology, Chemistry, Physics & Technology of Wood, vol. 58, Issue 1, pp. 82-90, 2004.
Vikman et al., "Kerr gated resonance Raman Spectroscopy in light fastness studies of ink jet prints", Vibrational Spectroscopy 37, 1, 2005.
Watanabe et al., "Fluorescence rejection in Raman spectroscopy by a gated single-photon counting method", Review of Scientific Instruments 56, 6, 1085.
Wolf et al, "Application of cheap lasers in shifted excitation Raman difference spectroscopy", J. Popp, W. Drexler, V.V. Tuchin and D.L. Matthews, Eds. (SPIE, Brussels, Belgium, 2012). p. 84271A.
Zhao et al., "Automated Fluorescence Rejection Using Shifted Excitation Raman Difference Spectroscopy", Applied Spectroscopy 56, 7, 834 (2002).
Xie et al., "Confocal micro-Raman spectroscopy of single biological cells using optical trapping and shifted excitation difference techniques", Journal of Applied Physics 93, 5, 2982 (2003).
Funfschilling et al., "CW Laser Wavelength Modulation in Raman and Site Selection Fluoresence Spectroscopy", Applied Spectroscopy 30, 4, 443 (1976).
Schreve et al., "Effective Rejection of Fluorescence Interference in Raman Spectroscopy Using a Shifted Excitation Diference Technique", Applied Spectroscopy 46, 4, 707 (1992).
Zou et al. "Fluorescence rejection by shifted excitation Raman difference spectroscopy", Proc. SPIE 7855, Copyright (C) 2011 American Chemical Society (ACS). All Rights Reserved., 78551M/1 (2010).
Michaelian et al., "Fluoresence rejection in Raman spectra of Syncrude Sweet Blend distillation fractions", Spectrochimica Acta Part A: Molecular & Biomolecular Spectroscopy 62, 1-3, 582 (2005).
Kamogawa et al., "Improved Fluorescence Rejection in Measurements of Raman Spectra of Fluorescent Compounds", Applied Spectroscopy. 42, 2, 248 (1988).
Maiwald et al., "Microsystem 671 nm light source for shifted excitation Raman difference spectroscopy", Applied Optics 48, 15, 2789 (2009).
Maiwald et al., "Rapid shifted excitation Raman difference spectroscopy with a distributed feedback diode laser emitting at 785 nm", Appl. Phys. B: Lasers Opt. 85, Copyright (C) 2011 American Chemical Society (ACS). All Rights Reserved., 509 (2006).
Chen et al., "Revisiting Raman lidar: application of new techniques to improve system performance", A. J. Sedlacek M. Ed. (SPIE, Denver, CO. USA, 1996), p. 182.
Osticioli et al., "Shift-Excitation Raman Difference Spectroscopy-Difference Deconvolution Method for the Luminescence Background Rejection from Raman Spectra of Solids Samples", Applied Spectroscopy 61, 8, 839 (2007).
Matousek et al., "Simple Reconstruction Algorithm for Shifted Excitation Raman Difference Spectroscopy", Applied Spectroscopy 59, 6, 848 (2005).
Stellman et al., "Suppression of fluorescence interference via wavelength shifted-keyed Raman spectroscopy using an argon ion laser and accusto-optic tunable filter", Spectrochimica Acta Part A: Molecular and Biomolecular Spectroscopy 54, 8, 1041 (1998).
Oshima et al., "Fluorescence-Suppressed Raman Techniques for Quantitative Analysis of Protein Solution using a Micro-Raman Probe, the Shifted Excitation Method, and Partial Least Squares Regression Analysis", Appl. Spectrosc. 60, Copyright (C) 2011 American Chemical Society (ACS). All Rights Reserved., 964 (2006).
Canetta et al., "Modulated Raman spectroscopy for enhanced indentification of bladder tumor cells in urine samples", Journal of Biomedical Optics 16, 3, 037002 (2011).
Masilu et al., "Modulated Raman Spectroscopy Technique for 'real-time' fluorescence rejection", Proc. SPIE 7568, Copyright (C) 2011 American Chemical Society (ACS). All Rights Reserved., 75680M/1 (2010).
De Luca et al., "Online Fluorescence Suppression in Modulated Raman Spectroscopy", Analytical Chemisty 82, 2, 738 (2010).
Mazilu et al., "Optimal algorithm for fluorescence suppression of modulated Raman spectroscopy". Opt. Express 18, 11, 11382 (2010).
Krafft et al., "Raman spectra of single cells with autofluorescence suppression by modulated wavelength excitation", A. Mahadevan-Jansen and W. Petrich, Eds. (SPIE. San Francisco, California, USA, 2012), p. 82190F.

* cited by examiner

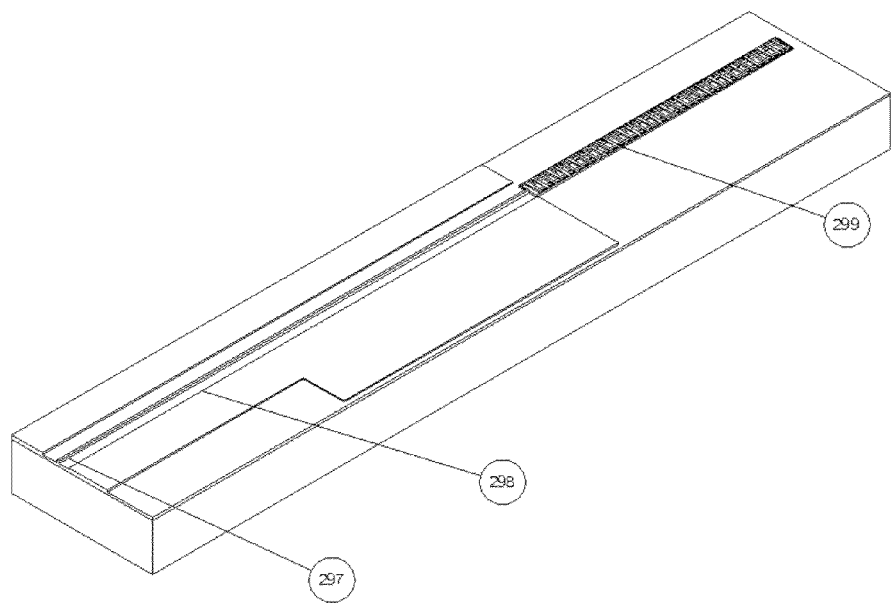
Figure 2A
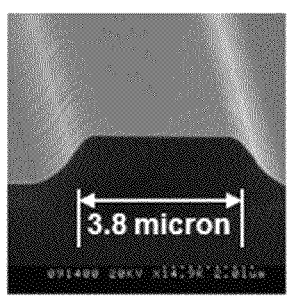   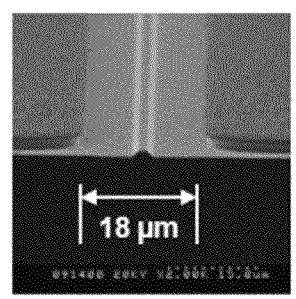   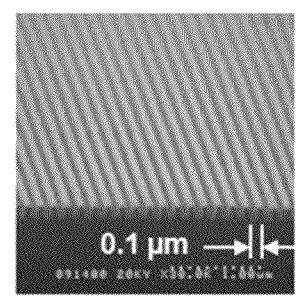
Figure 2B              Figure 2C              Figure 2D

METHOD AND APPARATUS FOR ACQUIRING RAMAN SPECTRA WITHOUT BACKGROUND INTERFERENCES

BACKGROUND

Prior Art

The following is a tabulation of prior art that presently appears relevant:

U.S. PATENTS

Klehr et. al.; "Method and Device for Producing a Raman Spectrum"; U.S. Pat. No. 7,864,311 B2; Date of Patent: Jan. 4, 2011

Brady et. al.; "Encoded Excitation Source Raman Spectroscopy Methods and Systems"; U.S. Pat. No. 7,002,679 B2; Date of Patent: Feb. 21, 2006

Tashiro et. al.; "Spectrometric Method and Apparatus for Spectrometry"; U.S. Pat. No. 5,946,090; Date of Patent: Aug. 31, 1999

Kane et. al.; "Determination of Fit Basis Functions"; U.S. Pat. No. 7,092,852 B1; Date of Patent: Aug. 15, 2006

Wang et. al.; "Method and System Removing Fluorescence and Other Slowly Varying Baseline in Raman Spectra"; U.S. Pat. No. 7,177,022 B2; Date of Patent: Feb. 13, 2007

Li et. al.; "Apparatus for Fluorescence Subtracted Raman Spectroscopy"; U.S. Pat. No. 7,145,651 B2; Date of Patent: Dec. 5, 2006

NON-PATENT LITERATURE

1. T. Hasegawa, J. Nishijo, and J. Umemura, Chemical Physics Letters 317, 6, 642 (2000).
2. Z. Jianhua, L. Harvey, I. M. David, and Z. Haishan, Applied Spectroscopy 61, 11, 1225 (2007).
3. Z. Jianhua, H. Lui, D. I. McLean, and Z. Haishan, Skin Research & Technology 14, 4, 484 (2008).
4. C. A. Lieber and A. Mahadevan-Jansen, Appl. Spectrosc. 57, 11, 1363 (2003).
5. P. A. Mosier-Boss, S. H. Lieberman, and R. Newbery, Appl. Spectrosc. 49, 5, 630 (1995).
6. D. Zhang and D. Ben-Amotz, Appl. Spectrosc. 54, 9, 1379 (2000).
7. I. G. Cormack, M. Mazilu, K. Dholakia, and C. S. Herrington, Applied Physics Letters 91, 2, 023903 (2007).
8. M. V. Schulmerich, R. Reddy, A. K. Kodali, L. J. Elgass, K. Tangella, and R. Bhargava, Analytical Chemistry 82, 14, 6273 (2010).
9. E. C. Le Ru, L. C. Schroeter, and P. G. Etchegoin, Analytical Chemistry 84, 11, 5074 (2012).
10. Benniston, C. A, Matousek, P, McCulloch, E. I, Parker, W. A, Towrie, and M, Journal of Physical Chemistry A 107, 22, 4347 (2003).
11. E. V. Efremov, J. B. Buijs, C. Gooijer, and F. Ariese, Appl. Spectrosc. 61, 6, 571 (2007).
12. N. Everall, T. Hahn, P. Matousek, A. W. Parker, and M. Towrie, Appl. Spectrosc. 55, 12, 1701 (2001).
13. V. E. Evtim, B. B. Joost, G. Cees, and A. Freek, Applied Spectroscopy 61, 6, 571 (2007).
14. A. Lakshmanna, B. Mallick, and S. Umapathy, Current Science (00113891) 97, 2, 210 (2009).
15. D. Mandal, M. Mizuno, and T. Tahara, Journal of Molecular Structure 735-736, 189 (2005).
16. D. V. Martyshkin, R. C. Ahuja, A. Kudriavtsev, and S. B. Mirov, Review of Scientific Instruments 75, 3, 630 (2004).
17. P. Matousek, M. Towrie, and A. W. Parker, J. Raman Spectrosc. 33, Copyright (C) 2011 American Chemical Society (ACS). All Rights Reserved., 238 (2002).
18. D. W. McCamant, P. Kukura, S. Yoon, and R. A. Mathies, Review of Scientific Instruments 75, 11, 4971 (2004).
19. A. K. Misra, S. K. Sharma, C. H. Chio, P. G. Lucey, and B. Lienert, Spectrochimica Acta Part A: Molecular and Biomolecular Spectroscopy 61, 10, 2281 (2005).
20. A. M. Saariaho, A. S. JäÄskelinen, P. Matousek, M. Towrie, A. W. Parker, and T. Vuorinen, Holzforschung: International Journal of the Biology, Chemistry, Physics, & Technology of Wood 58, 1, 82 (2004).
21. K. Vikman, H. litti, P. Matousek, M. Towrie, A. W. Parker, and T. Vuorinen, Vibrational Spectroscopy 37, 1, 123 (2005).
22. J. Watanabe, S. Kinoshita, and T. Kushida, Review of Scientific Instruments 56, 6, 1195 (1985).
23. S. Wolf and H. Doring, "Application of cheap lasers in shifted excitation Raman difference spectroscopy", J. Popp, W. Drexler, V. V. Tuchin and D. L. Matthews, Eds. (SPIE, Brussels, Belgium, 2012), p. 84271A.
24. J. Zhao, M. M. Carrabba, and F. S. Allen, Appl. Spectrosc. 56, 7, 834 (2002).
25. C. Xie and Y.-q. Li, Journal of Applied Physics 93, 5, 2982 (2003).
26. J. Funfschilling and D. F. Williams, Appl. Spectrosc. 30, 4, 443 (1976).
27. A. P. Shreve, N. J. Cherepy, and R. A. Mathies, Appl. Spectrosc. 46, 4, 707 (1992).
28. W. Zou, Z. Cai, and J. Wu, Proc. SPIE 7855, Copyright (C) 2011 American Chemical Society (ACS). All Rights Reserved., 78551M/1 (2010).
29. K. H. Michaelian, H. Yuan, R. H. Hall, and J. T. Bulmer, Spectrochimica Acta Part A: Molecular & Biomolecular Spectroscopy 62, 1-3, 582 (2005).
30. K. Kamogawa, T. Fujii, and T. Kitagawa, Appl. Spectrosc. 42, 2, 248 (1988).
31. M. Maiwald, H. Schmidt, and B. Sumpf, Applied Optics 48, 15, 2789 (2009).
32. M. Maiwald, G. Erbert, A. Klehr, H. D. Kronfeldt, H. Schmidt, B. Sumpf, and G. Traenkle, Appl. Phys. B: Lasers Opt. 85, Copyright (C) 2011 American Chemical Society (ACS). All Rights Reserved., 509 (2006).
33. C. G. Chen and A. J. Sedlacek Iii, "Revisiting Raman lidar: application of new techniques to improve system performance", A. J. Sedlacek Iii, Ed. (SPIE, Denver, Colo., USA, 1996), p. 182.
34. I. Osticioli, A. Zoppi, and E. M. Castellucci, Appl. Spectrosc. 61, 8, 839 (2007).
35. P. Matousek, M. Towrie, and A. W. Parker, Appl. Spectrosc. 59, 6, 848 (2005).
36. C. M. Stellman and F. Bucholtz, Spectrochimica Acta Part A: Molecular and Biomolecular Spectroscopy 54, 8, 1041 (1998).
37. Y. Oshima, Y. Komachi, C. Furihata, H. Tashiro, and H. Sato, Appl. Spectrosc. 60, Copyright (C) 2011 American Chemical Society (ACS). All Rights Reserved., 964 (2006).
38. E. Canetta, M. Mazilu, A. C. De Luca, A. E. Carruthers, K. Dholakia, S. Neilson, H. Sargeant, T. Briscoe, C. S. Herrington, and A. C. Riches, Journal of Biomedical Optics 16, 3, 037002 (2011).
39. M. Mazilu, L. A. C. De, A. Riches, S. Herrington, K. Dholakia, D. L. Farkas, D. V. Nicolau, and R. C. Leif, Proc. SPIE 7568, Copyright (C) 2011 American Chemical Society (ACS). All Rights Reserved., 75680M/1 (2010).

40. A. C. De Luca, M. Mazilu, and A. Riches, Analytical Chemistry 82, 2, 738 (2010).
41. M. Mazilu, A. C. De Luca, A. Riches, C. S. Herrington, and K. Dholakia, Opt. Express 18, 11, 11382 (2010).
42. C. Krafft, S. Dochow, N. Bergner, J. H. Clement, B. B. Praveen, M. Mazilu, R. Marchington, K. Dholakia, and J. Popp, "Raman spectra of single cells with autofluorescence suppression by modulated wavelength excitation", A. Mahadevan-Jansen and W. Petrich, Eds. (SPIE, San Francisco, Calif., USA, 2012), p. 82190F.

Although Raman spectroscopy is a powerful analytical method for molecular analysis, Raman spectra are often plagued with intense fluorescence backgrounds resulting from impurities or from the population of a sample's excited state(s). The use of long wavelength lasers such as the 1064 nm Nd:YAG laser commonly used for FT-Raman spectroscopy results in a significant reduction in fluorescence backgrounds. However, since the Raman scattering is inversely proportional to $\lambda^4$ for the excitation laser, it also results in less Raman signal and thus often requires the use of longer acquisition times and higher laser powers which can often lead to sample burning. In addition, FT-Raman instruments are typically large and expensive with integral interferometers which are sensitive to mechanical vibration. For these reasons FT-Raman spectroscopy does not easily lend itself to applications involving process control or remote deployment. Alternatively, dispersive Raman instruments using CCD detection with solid state laser excitation provide a robust no moving parts option; however, the use of shorter wavelength excitation required for CCD detection in these systems results in significantly more fluorescence. For this reason, several methods have been developed to extract the Raman information from interfering backgrounds. Overall, these methods of removing fluorescence can be separated into four categories: algorithm based baseline correction methods; methods and devices using specialized sampling optics; time gating methods; and shifted excitation methods.

Algorithm-based methods attempt to mathematically estimate a baseline and then subtract the estimated baseline from the Raman spectrum to give a fluorescence free spectrum. Algorithm-based methods suffer from the requirement that they cannot be universally applied to all types of fluorescence without either significant degradation in performance or significant user intervention to adjust sensitive algorithm parameters. One reason for this disadvantage is the varied nature of fluorescence backgrounds. Another reason is due to the complexity of the fitting algorithms. This prevents these methods from being used routinely by non-technical personnel. Methods using algorithm based baseline corrections are described in detail in the peer-reviewed scientific literature[1-6]. Also, Kane et al. (U.S. Pat. No. 7,092,852) and Wang et al. (U.S. Pat. No. 7,177,022) describe methods for estimating baselines in Raman spectra.

Methods using unique sampling optics and geometries have the disadvantage of only mitigating the impact of fluorescence instead of completely eliminating it from the Raman spectrum. These methods also suffer from the disadvantage of only being applicable to certain types of samples. For instance, some of these methods can only be used on solids or only be used on liquids. Methods using unique sampling optics and geometries are described in detail in the peer-reviewed scientific literature[7-9].

Time gating methods involve using time to discriminate between the Raman signal (which occurs on a fast time scale) and the fluorescence (which generally occurs on a slower timescale). Since the time scale discrimination required for these methods is on the order of picoseconds to nanoseconds, the methods involve the use of either: 1) complex, bulky, and expensive instrumentation or 2) instrumentation which requires excessively long periods of time to collect an entire Raman spectrum. Also, these methods are not universally successful for all samples due to the varied nature of fluorescence decay times. These methods also have the disadvantage of not being able to remove spectral backgrounds which arise from optical processes which occur on the same timescale as Raman. Such processes include stray light scatter, fixed pattern noise arising from a detector array, room lights, cosmic rays, and other extraneous sources of optical interference. These methods also have the disadvantage of requiring the Raman to be generated using a pulsed laser source. This results in a large number of Joules being delivered to the sample in a short period of time and often results in sample burning. Examples of time gating methods are described in detail in the peer-reviewed scientific literature[10-22].

All shifted excitation methods involve changing the excitation laser during spectral acquisition. These methods rely on a common concept: the location of Raman intensities in spectral space changes with excitation while unwanted spectral intensities corresponding to fluorescence, stray light, fixed pattern detector noise etc., remain unchanged in spectral space. The difference in the various methods to date occurs in how the spectra are acquired and how the Raman data is extracted. The simplest extraction method is taking a difference between two sets of excitation data and is referred to as Shifted Excitation Raman Difference Spectroscopy (SERDS) and only requires excitation at two distinct wavelengths. This type of method has two distinct disadvantages: 1) random noise in two measurements is increased during subtraction; 2) the result is a derivative spectrum instead of a true Raman spectrum in spectral space. Since a true Raman spectrum is not generated, the data is not easily interpreted. Another disadvantage of SERDS is that there is significant difficulty in reconstructing the Raman spectrum from the derivative data. The reconstruction requires the use of advanced algorithms which have to be applied appropriately for specific samples since one set of algorithm parameters will not work universally for all samples. Since this method has been in use for over thirty years, there are many examples of its application in the peer-reviewed scientific literature[23-36].

Li et al. (U.S. Pat. No. 7,145,651) has described a device for SERDS which utilizes an acoustic optical tunable filter and laser to generate the two excitation wavelengths. Tashiro et al. (U.S. Pat. No. 5,946,090) has described a device for SERDS which utilizes an acoustic optical tunable filter and laser to generate the two laser wavelengths with phase sensitive detection of the Raman utilizing single photodiodes. Klehr et al. (U.S. Pat. No. 7,864,311) has described a way to perform SERDS using a diode laser to generate the two excitation wavelengths by modulating the injection current of the diode laser between two values. All of these methods suffer from the disadvantages of SERDS in general, i.e., increased noise and output which is in derivative form.

There are three previous methods using shifted excitation which utilize more than 2 excitation sources to generate the Raman spectra. These methods are generally referred to as Modulated Raman Spectroscopy, Encoded Excitation Source Raman Spectroscopy, and Shifted Excitation Raman Spectroscopy. The existing embodiments of these three methods are described below along with their disadvantages.

A Shifted Excitation method which involves more than 2 lasers is described by De Luca et al. (Analytical Chemistry 82, 2, 738, 2010) and is often referred to as Modulated Raman Spectroscopy. In this method, a complex tunable laser is used to generate the Raman signal. The laser excitation wavelength is modulated by scanning the external grating of a 785 nm tunable laser at a set frequency between two limiting grating positions. This results in the sample being illuminated with monochromatic laser radiation which is being modulated between two limiting wavelengths. The difference in photon energy between the two lasers at the limiting positions of the grating is stated as approximately 60 GHz. This means that the two limiting wavelengths of the laser are typically 785 nm and 785.123 nm. Although the frequency of the tunable laser grating (ie., the time it takes to complete a cycle between the limiting wavelengths) is set for a particular experiment, results are given at modulation frequencies between 0.005-0.4 Hz. While the modulating laser is irradiating the sample, a spectrometer with a CCD is used to asynchronously collect the Raman spectra. The typical integration time of the CCD is reported as 100 ms. In addition, there is a delay between when the CCD completes one acquisition of a Raman spectrum and when it can begin another acquisition of a Raman spectrum. This delay is typically 80 ms but is variable because it includes the time it takes to readout the spectrum in digital form to a computer. Taken together, the total CCD acquisition frequency is approximately 5 Hz. The net result is that the laser modulation and the CCD acquisition are asynchronous. Because of this asynchronicity, an involved calibration procedure is required for each instrument in order to determine what excitation frequency was used for the recorded Raman spectra. The first step of this calibration procedure is to synchronize the laser modulation with the CCD acquisition rate. This is done by first determining the exact frequencies of the two events and then calculating the delay between them. The delay is then used to synchronize the two events. The second part of the calibration involves creating a calibration curve relating the laser grating position (which determines the laser wavelength) to the delay. Once this procedure is accomplished, the modulated Raman spectra are used to construct a differential Raman spectrum by using a least squares routine to solve for the Raman spectra at the two limiting wavelengths and then taking the difference between the two Raman spectra. Alternative, it has been shown that the differential Raman spectrum can be constructed using Principal Component Analysis. As described above, when acquiring the modulated Raman spectra, the modulation frequency of the laser could be varied between 0.005-0.4 Hz. As stated by the De Luca, the lower range on this frequency results in the generation of SERDS data (ie., data is only being collected at the two limiting laser excitation wavelengths which is the defining case for SERDS). The higher range of the modulation frequency is limited by the capabilities of the tunable laser (maximum scan rate of the grating) and by the fact that it cannot exceed the acquisition rate of the CCD detector.

Although Modulated Raman Spectroscopy offers significant advantages over SERDS at higher modulation rates of the excitation laser, it suffers from notable drawbacks:

1) As with SERDS, the final result is a derivative spectrum and not the true Raman spectrum of the sample.
2) A tunable laser with a triggered external grating is required. Conventionally these lasers are expensive and are too large to be used for portable instruments.
3) The method requires an involved calibration procedure which is specific to the laser being used, the CCD being used, the integration time being used, the modulation frequency being used, and the limiting excitation wavelengths being used.
4) The method requires a CCD which can be run at a set and predetermined frequency.
5) The delay between CCD acquisitions (80 ms) is on the scale of the CCD integration time (100 ms). This results in almost half of the experimental time NOT being used to collect the Raman signal which in effect almost doubles the acquisition time required to obtain a prescribed Raman signal level.
6) The improvement in signal-to-noise over SERDS is realized at higher modulation rates of the laser, but this has a practical limit due to the limitations of tunable lasers and due to the fact that the modulation rate of the laser cannot exceed the acquisition rate of the CCD.

There are several examples of this method in the peer-reviewed scientific literature[37-42].

A second example of shifted excitation using more than two excitation wavelengths is given by Brady et al. (U.S. Pat. No. 7,002,679). Brady describes a method referred to as Encoded Excitation Source Raman spectroscopy. In this method, an array of discrete excitation sources with varying wavelengths is used to generate Raman by turning on selected combinations of the sources based on an encoding pattern such as Walsh or Hadamard encoding. In order to extract the Raman spectrum from the resulting signals, Brady describes setting up a system of linear equations relating the pure Raman spectrum and the pure non-Raman spectrum to the acquired signals and the encoding pattern. For simple encoding patterns, Brady describes using a least-squares procedure to extract the Raman spectrum. For more complex encoding, a Hadamard transform (or similar transform) is described. In these embodiments, Encoded Excitation Source Raman suffers from the fact that multiple excitation sources are required. This requirement for multiple excitation sources greatly increases the complexity and expense of the apparatus. For example, in one embodiment, Brady describes using various combinations of four lasers at wavelengths of 827.03 nm, 827.78 nm, 829.33 nm, and 831.78 nm. There are several additional disadvantages to this method. One disadvantage is that it is very difficult if not impossible to mass produce articles conforming to this embodiment with the exact same laser excitation wavelengths. The result of this is that each subsequent article of manufacture will require a unique system of linear equations to be tailored specifically for that subsequent article of manufacture. Another disadvantage is that since the resolution of the resulting Raman spectrum is dependent upon the wavelength spacing of the lasers, subsequent articles of manufacture will offer varying degrees of quality in terms of the Raman spectra they produce. In another embodiment, Brady describes the use of a broad band source and a tunable filter with a programmable pattern generator to produce the combinations of excitation sources. This embodiment still suffers from the disadvantage of requiring complex and expensive instrumentation. In addition, this embodiment will result in lower quality Raman spectra in terms of signal to noise since a filtered broadband source cannot deliver the same optical power as a monochromatic laser. This is well known by those experienced in the art of Raman spectroscopy. As an example, in one embodiment Brady describes the use of a super-luminescent diode as the broadband source. If such a source were filtered to a wavelength band which approached the bandwidth of the Raman peaks (which is a requirement for resolved spectra) its intensity would be orders of magnitude less than a single-mode diode laser (monochromatic laser) of equivalent optical output.

Willet et al. describes the third method of Shifted Excitation using more than two lasers (Opt. Express 16, 15, 10975, 2008). In this embodiment, a series of diode lasers at closely spaced wavelengths are used for the acquisition of shifted Raman spectra. The multiple discrete lasers are used to irradiate a sample in a serial fashion. The instrument used included eight single-mode excitation lasers with fixed wavelengths of 782.6 nm, 784.1 nm, 784.4 nm, 786.8 nm, 788.6 nm, 790.7 nm, 793.6 nm, and 794.3 nm. In their embodiment, three or more of the lasers are used to collect the Raman spectra of a sample. The collected Raman spectra are used to reconstruct the true Raman spectrum of the sample without fluorescence using an expectation maximization algorithm. The algorithm is used to solve a system of linear equations where there are a number of possible solutions. For processed spectra which contain N wavenumber positions and K excitation lasers, the system of linear equations can be described as:

$$y = HS \quad (1)$$

where y is a column vector of length N×K containing the acquired spectra using each excitation source;

$$S = [S_{NR}, S_R]^T \quad (2)$$

where $S_{NR}$ is the signal due to the non-Raman events such as fluorescence and $S_R$ is the signal due to Raman and "T" indicates the transpose; and $$H \equiv \begin{bmatrix} H_F & H_{R1} \\ \vdots & \vdots \\ H_F & H_{RK} \end{bmatrix} \quad (3)$$

where $H_F$ is a N×N identity matrix, $H_{R1}$ is a N×N identity matrix, $H_{Rk}$ is a N×N matrix similar to $H_F$ except all unity values are shifted by the wavenumber shift of the $k^{th}$ laser relative to the first $1^{st}$ laser. Hence $H_{R1} = H_F = I$. Keeping this in mind, the matrix H is a 2N×NK matrix. Most dispersive Raman spectrometers utilize CCD detectors with 1024 or more detection elements. In this case, H would consist of 6,291,456 elements when only 3 excitations are used. For this reason, using equation 1 to solve for the pure Raman spectrum is computationally burdensome whether carried out using a Lucy-Richardson formula, or by explicitly solving using a least-squares approach.

Although Shifted Excitation Raman spectroscopy offers significant advantages over SERDs, it suffers from notable drawbacks:

1) Each desired excitation source requires the addition of a wavelength stabilized laser to the system resulting in an increase in system cost and complexity with each additional excitation source.
2) The close wavelength spacing of the lasers is obtained using diode lasers stabilized with externally mounted holographic gratings. Using this approach, a uniform wavelength spacing between the excitation lasers is not possible unless custom lasers are made and then only at great expense. Even if that were obtained for one article of manufacture, duplicating it for a second article of manufacture would be very difficult and expensive.
3) Once an article of manufacture is made, the method is limited to the number of existing excitation lasers.
4) Once an article of manufacture is made, the wavelength separation between lasers cannot be adjusted.
5) The importance of 2, 3, and 4 cannot be overstated since the quality of the Raman spectra is dependent upon the selection of an optimum number of excitation lasers and an optimum wavelength spacing of the lasers and these optima are often dependent on experimental conditions such as the allowable acquisition time of each spectrum, the bandwidth or resolution of each spectrum, the Raman cross-section of the sample, the amount of interfering fluorescence, and the spectral range.
6) The suggested method of processing the data is intensive and time-consuming. This is evidenced by the fact that suggested methods of data compression (Haar Tree Pruning) are included in the article in order to decrease the processing time.
7) The method does not provide a way producing articles of manufacture which all have the same wavelength spacing of the excitation lasers. This requires each article of manufacture to have a unique algorithm for extracting the Raman data.
8) The number of calculations required to extract the Raman spectrum is proportional to K×N×N, where K is the number of excitation sources and N is the number of spectral positions.

SUMMARY

In accordance with one embodiment, a Raman spectrometer in a handheld format, comprising a temperature-controlled diode laser with Bragg grating optical feedback provides for the acquisition of a plurality of sequentially shifted excitation Raman spectra which are processed according to additional embodiments to eliminate fluorescence backgrounds, fixed pattern noise, and room lights, while maintaining the Raman data in true spectral space and thereby avoiding generation of derivative or difference spectra.

Advantages

Accordingly, several advantages of one or more aspects are as follows: to rapidly extract Raman spectra from fluorescence interference using inexpensive and compact instrumentation and efficient data processing; that is not limited by the sample being analyzed; that offers superior S/N performance when compared to previous methods; that requires sub-second data processing times as opposed to previous methods where data processing times exceed a minute; that results in Raman spectra whose peak positions are independent of the selected excitation shifts; that embodies an article of manufacture which can be used to easily vary all of the excitation conditions in a defined manner (number of excitations, separation of excitations, and integration time of each excitation) in order to obtain optimal results; that even in the absence of a fluorescence background improves the S/N ratio by reducing random shot and thermal noise and by eliminating fixed pattern and random spike noise; and that allows a single processing algorithm with set parameters to be used for multiple articles of manufacture.

DRAWINGS

Figures

FIG. 1. This figure shows a schematic diagram of a Raman spectrometer according to embodiments of the present invention comprising a 785 nm DBR diode laser (100); asphere collimation lens (101); laser band-pass filter (103); dichroic-beamsplitter (104); asphere focusing lens (102); long pass filter (105); doublet achromat focusing lens (106); rectangular slit (107); doublet achromat collimating lens (108); long pass filter (109); 1500 groove/mm volume holographic transmission grating (110); doublet achromat focusing lens (111); CCD detector (112); CCD control board (113); thermoelectric controller/laser diode driver board (114).

FIG. 2. This figure shows A) a diagram of a distributed Bragg reflector (DBR) diode laser 300 with SEM micrographs showing in detail B) the emitting facet of the laser cavity 297; C) the laser cavity and electrical pads 298; and D) the Bragg grating 299.

Figure 3A:
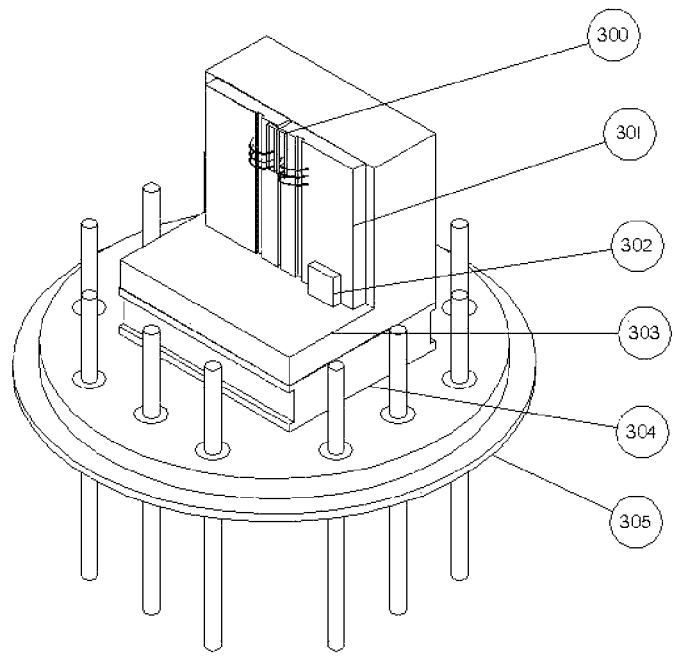
Figure 3B:
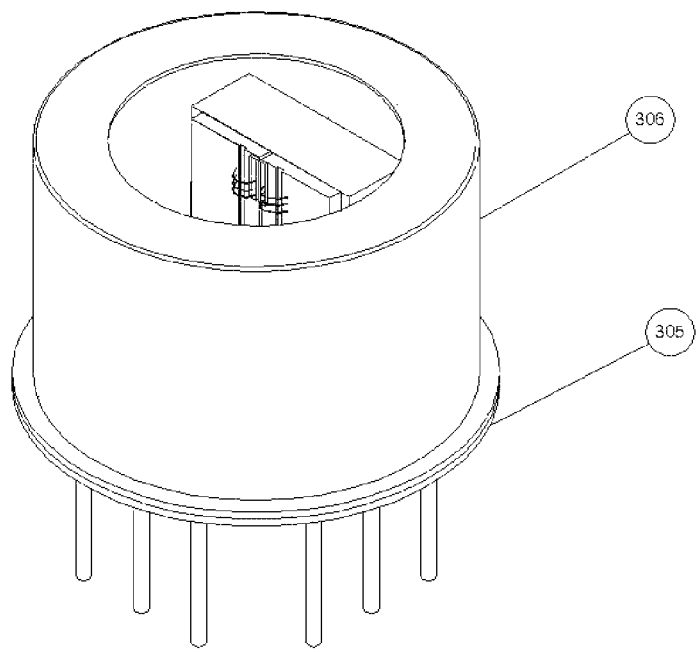

FIG. 3. This figure shows two schematics with detail of 100 A) shown without cover and B) with a T08 cover with an optical window.

Figure 4:
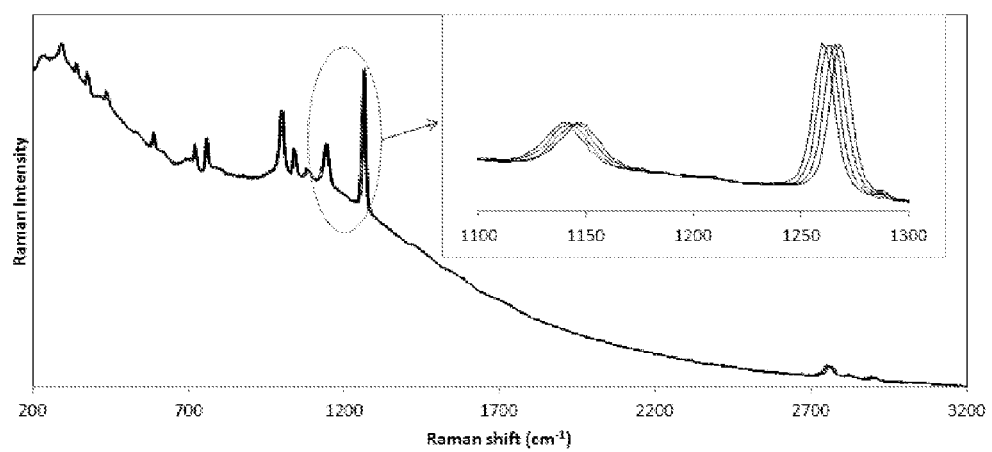

FIG. 4. This figure shows the Raman spectra of dimethyl glyoxime acquired at four DBR laser temperatures (20, 23, 26, and 29° C.) with a CCD integration time of 0.8 s for each spectrum and a laser power of 50 mW. The change in laser temperature results in a shift of 3.60 $cm^{-1}$ for each of the Raman spectra while the underlying background remains unchanged (as shown in the inset).

Figure 5:
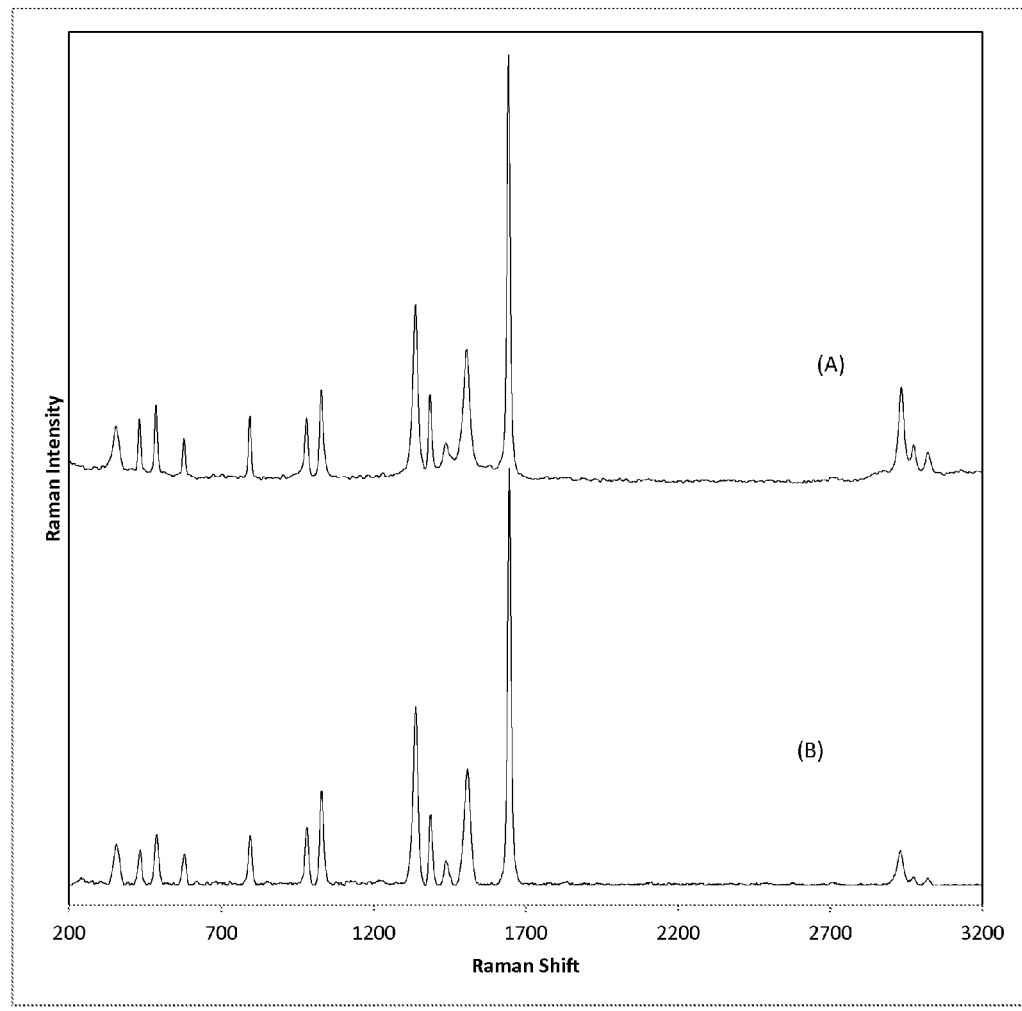

FIG. 5. This figure shows a graph comparing a FT-Raman spectrum to a Raman spectrum extracted from sequentially shifted excitation Raman spectra. (A) FT-Raman spectrum of dimethyl glyoxime acquired using a 1064 nm laser. The spectrum was acquired with an integration time of 120 s and a laser power of 800 mW. (B) Raman spectrum of dimethyl glyoxime which is obtained using the 4 sequentially shifted excitation Raman spectra of dimethyl glyoxime shown in FIG. 4.

Figure 6:
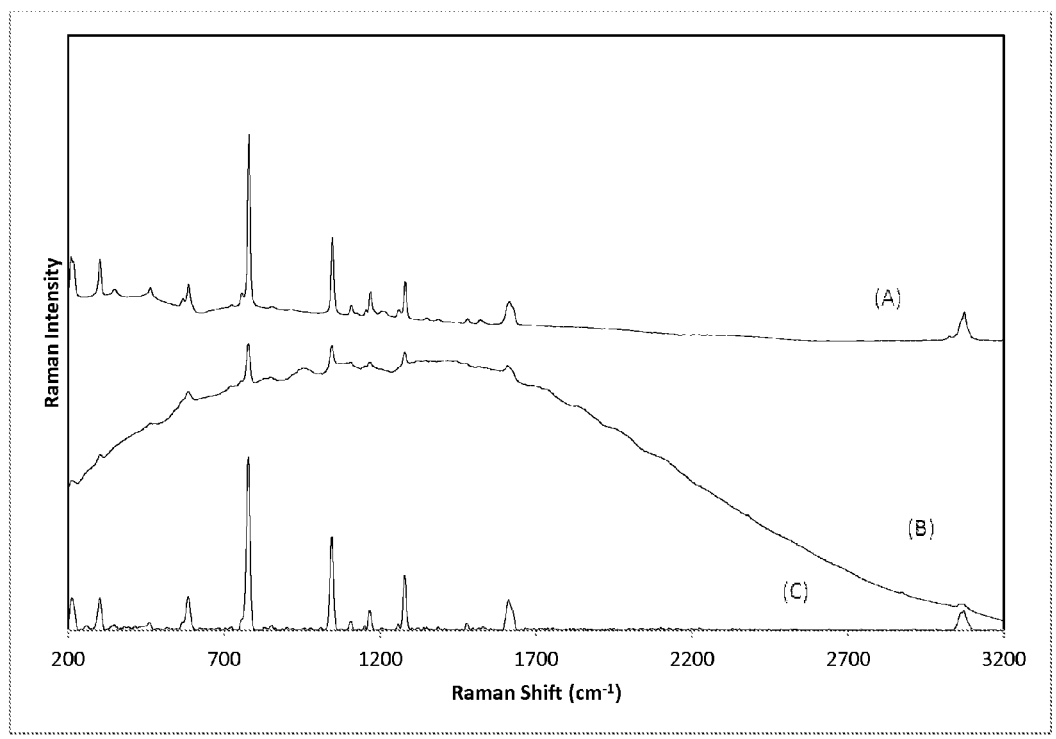

FIG. 6. This figure shows a graph comparing embodiments of the present invention to FT-Raman spectroscopy and Dispersive Raman spectroscopy. (A) FT-Raman spectrum of Catechol acquired using 1064 nm laser (120 s acquisition and 800 mW). (B) Dispersive Raman spectrum of Catechol acquired using 785 nm laser at 20° C. (2.5 s acquisition and 50 mW). (C) Raman spectrum of Catechol obtained by processing sequentially shifted excitation Raman spectra acquired at three laser temperatures 23.2, 26.5, and 29.1 C (2.5 s×3 acquisition and 50 mW).

Figure 7:
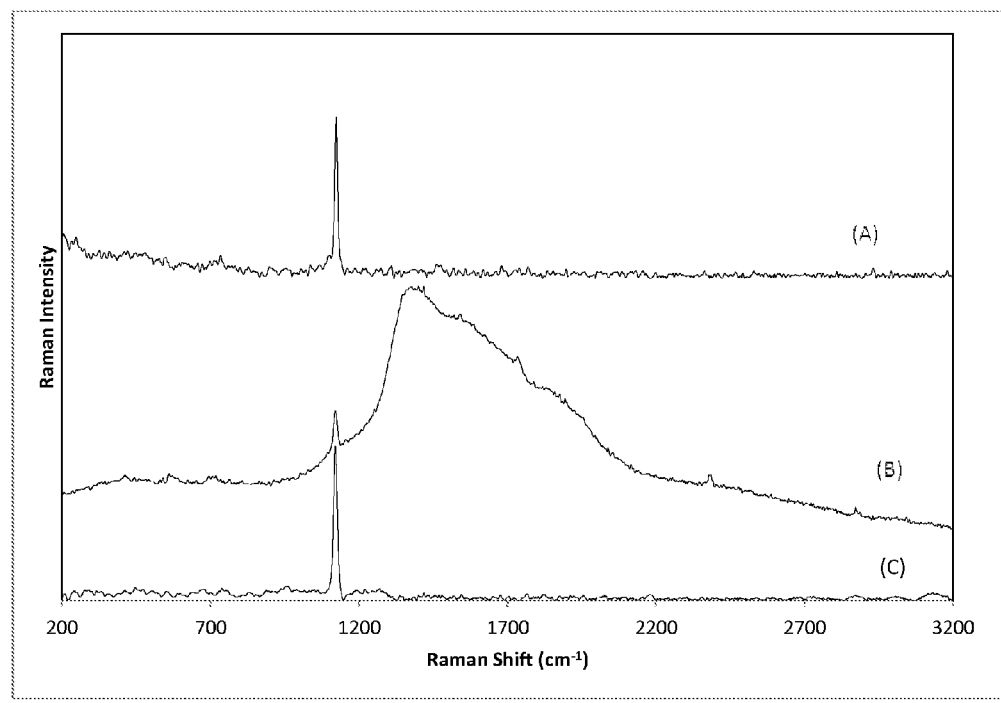

FIG. 7. This figure shows a graph comparing embodiments of the present invention to FT-Raman spectroscopy and Dispersive Raman spectroscopy. (A) FT-Raman spectrum of Magnesium Carbonate acquired using 1064 nm laser (120 s acquisition and 800 mW). (B) Dispersive Raman spectrum of Magnesium Carbonate acquired using 785 nm laser at 20° C. (3 s acquisition and 50 mW). (C) Raman spectrum of Magnesium Carbonate obtained by processing sequentially shifted excitation Raman spectra acquired at five laser temperatures: 20, 23, 26, 29, and 32 C (3 s×5 acquisitions and 50 mW).

Figure 8:
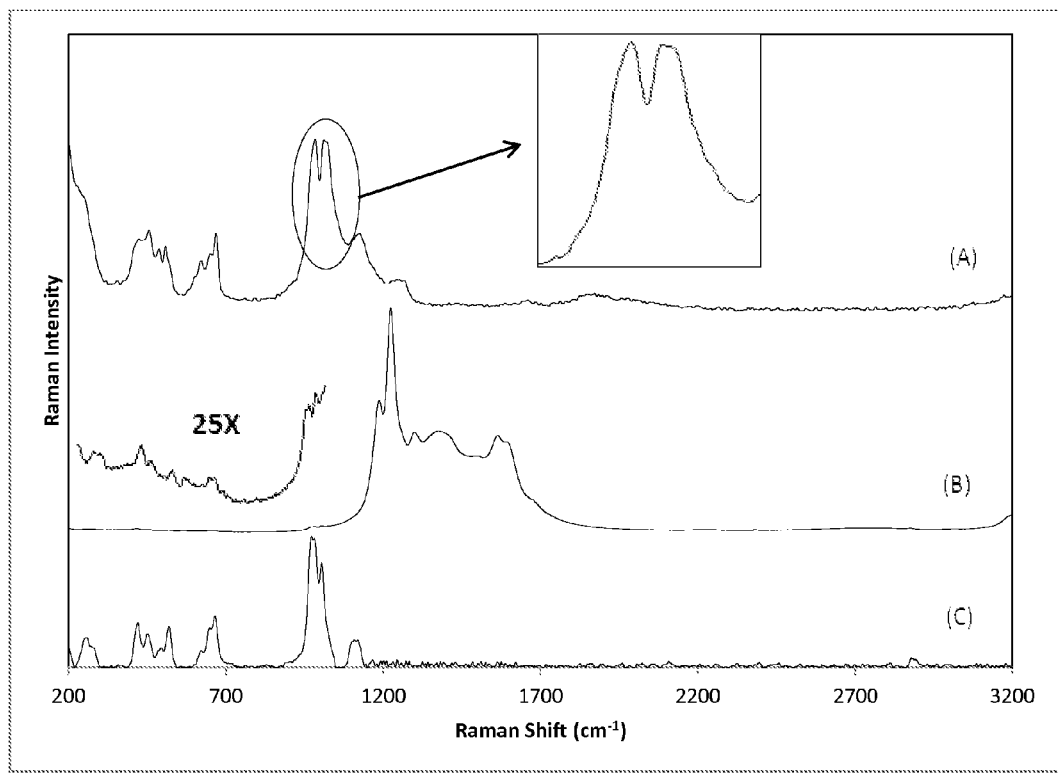

FIG. 8. This figure shows a graph comparing embodiments of the present invention to FT-Raman spectroscopy and Dispersive Raman spectroscopy (A) FT-Raman spectrum of Ceric Ammonium Sulfate acquired using 1064 nm laser (120 s acquisition and 800 mW). (B) Dispersive Raman spectrum of Ceric Ammonium Sulfate acquired using 785 nm laser at 20° C. (4 s acquisition and 50 mW). (C) Raman spectrum of Ceric Ammonium Sulfate obtained using sequentially shifted excitation Raman spectra acquired at five laser temperatures: 17, 20, 23, 26, and 29 C (4 s×5 acquisitions and 50 mW).

Figure 9:
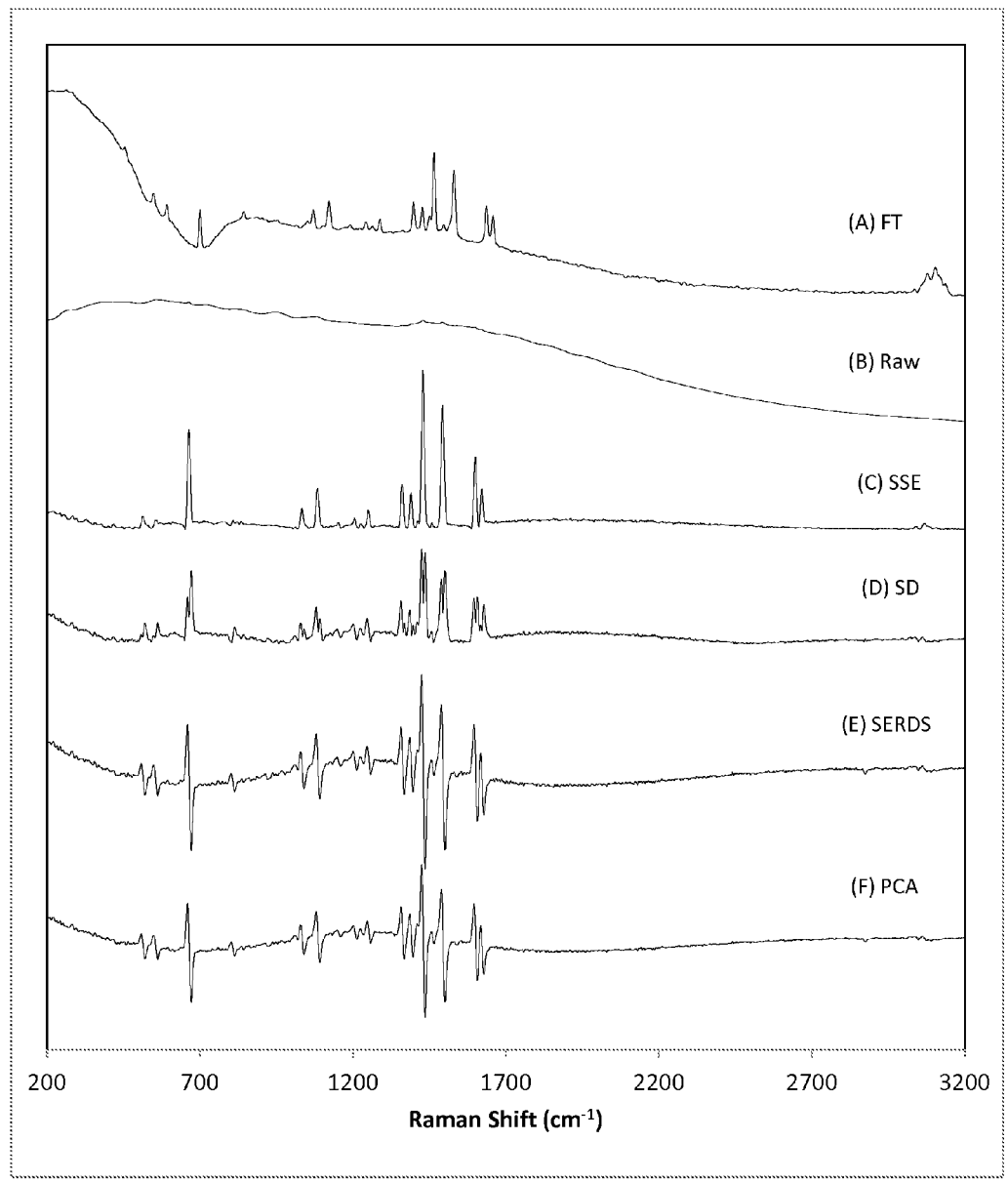

FIG. 9. This figure shows a graph comparing Dispersive Raman spectroscopy, SERDS and FT-Raman spectroscopy to embodiments of the present invention (A) FT-Raman spectrum of acenaphthylene acquired using 1064 nm laser (120 s acquisition and 800 mW). (B) Dispersive Raman spectrum of acenaphthylene acquired using 785 nm laser at 20° C. (10 s acquisition and 50 mW). (C) Raman spectrum of acenaphthylene obtained from iterative processing of shifted excitation Raman spectra. (D) Standard deviation Raman spectrum of acenaphthylene obtained from shifted excitation Raman spectra. (E) SERDS spectrum of acenaphthylene obtained by acquiring only two shifted excitation spectra (20 and 29 C and 10 s×2 acquisition). (F) Raman spectrum of acenaphthylene obtained using PCA to process shifted excitation Raman spectra. All C,D, and F were determined using spectral data acquired at four laser temperatures: 20, 23, 26, and 29 C (10 s×4 acquisition and 50 mW).

Figure 10:
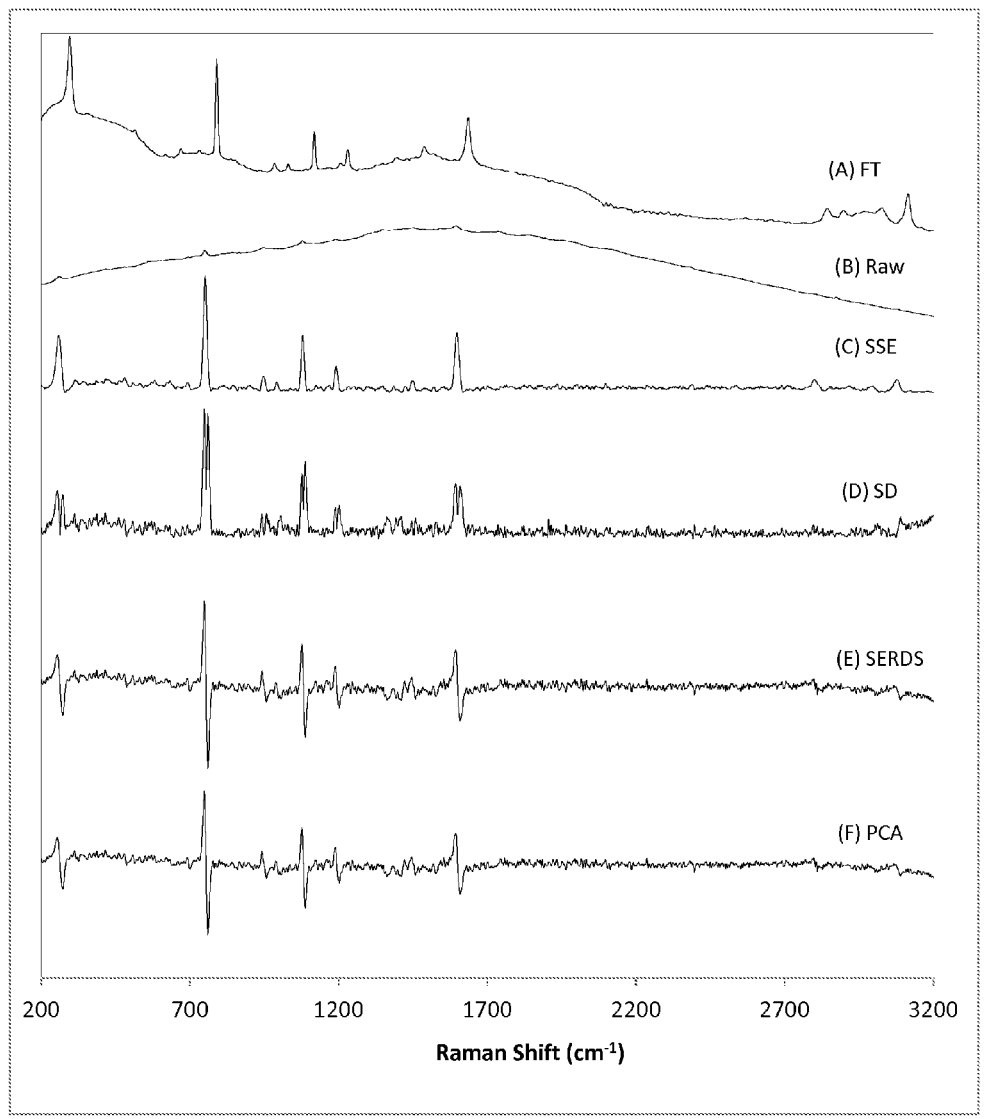

FIG. 10. This figure shows a graph comparing Dispersive Raman spectroscopy, SERDS and FT-Raman spectroscopy to embodiments of the present invention. (A) FT-Raman spectrum of 4-Bromo-N, N-dimethyl-aniline acquired using 1064 nm laser (120 s acquisition and 800 mW). (B) Dispersive Raman spectrum of 4-Bromo-N, N-dimethyl-aniline acquired using 785 nm laser at 20° C. (5.2 s acquisition and 50 mW). (C) Raman spectrum of 4-Bromo-N, N-dimethyl-aniline obtained from iterative processing of shifted excitation Raman spectra. (D) Standard deviation Raman spectrum of 4-Bromo-N, N-dimethyl-aniline obtained from shifted excitation Raman spectra. (E) SERDS spectrum of 4-Bromo-N, N-dimethyl-aniline obtained by acquiring only two shifted excitation spectra (20 and 29 C and 5.2 s×2 acquisition). (F) Raman spectrum of 4-Bromo-N, N-dimethyl-aniline obtained using PCA to process shifted excitation Raman spectra. All C,D, and F were determined using spectral data acquired at four laser temperatures: 21, 24, 27, and 30 C (5.2 s x×4 acquisition and 50 mW).

Figure 11:
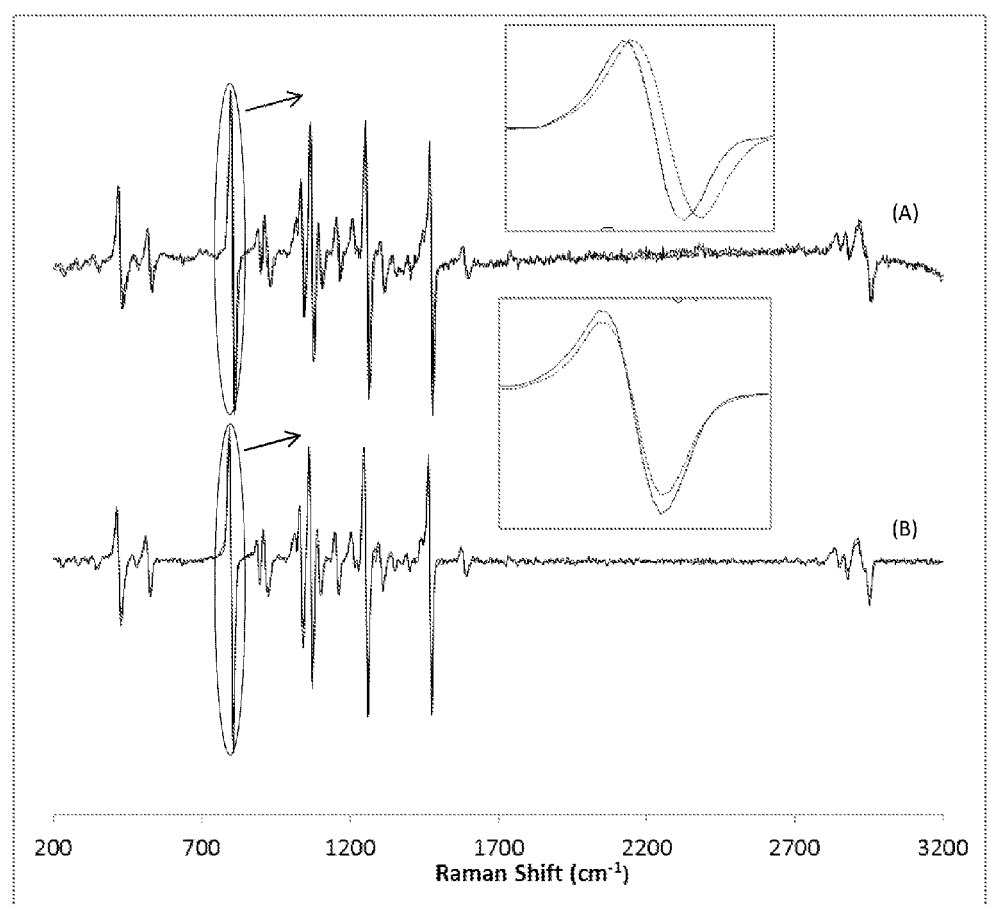

FIG. 11. Each figure shows a graph of Raman data of tris(hydroxymethyl) aminoethane extracted from shifted excitation Raman spectra acquired using two temperature profiles: 20, 23, and 26° C. (solid line), and 20, 26, 32° C. (dotted line). The acquisition time was 1 s×3. (A) PCA extracted Raman spectra. (B) Derivatives of iteratively extracted Raman spectra.

Figure 12:
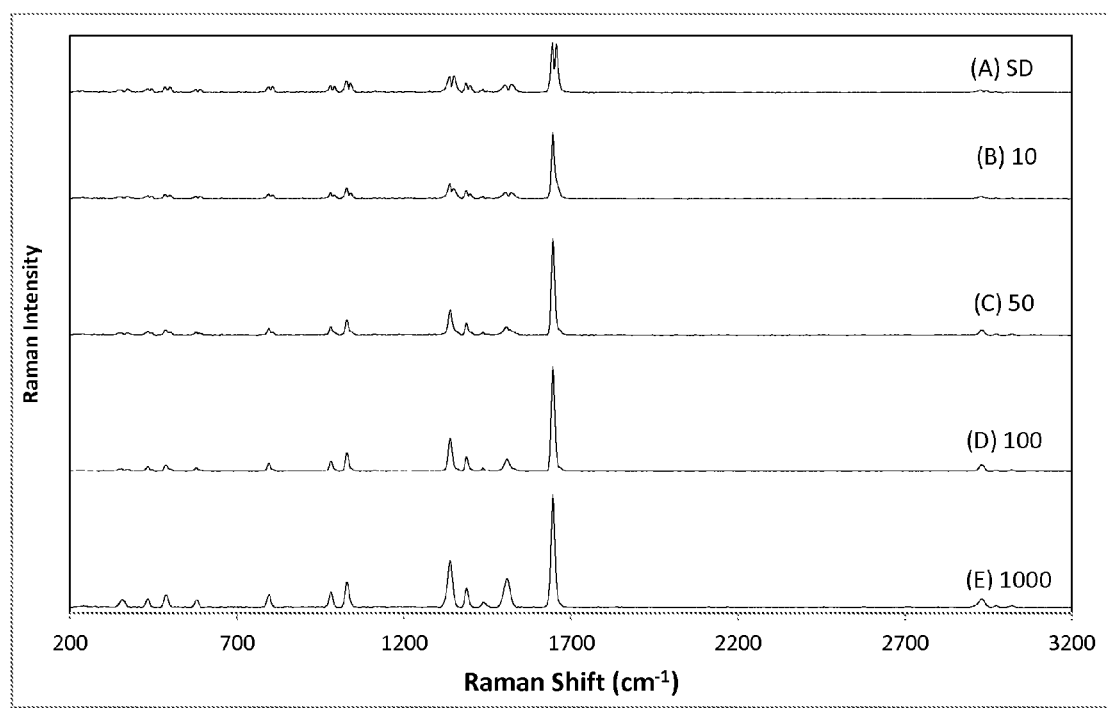

FIG. 12. This figure shows Raman spectra of dimethyl glyoxime extracted from shifted excitation Raman spectra using various numbers of iterations according to embodiments of the present invention; (A) standard deviation Raman spectrum (0 iterations), (B) 10 iterations, (C) 50 iterations, (D) 100 iterations, and (E) 1000 iterations.

Figure 13:
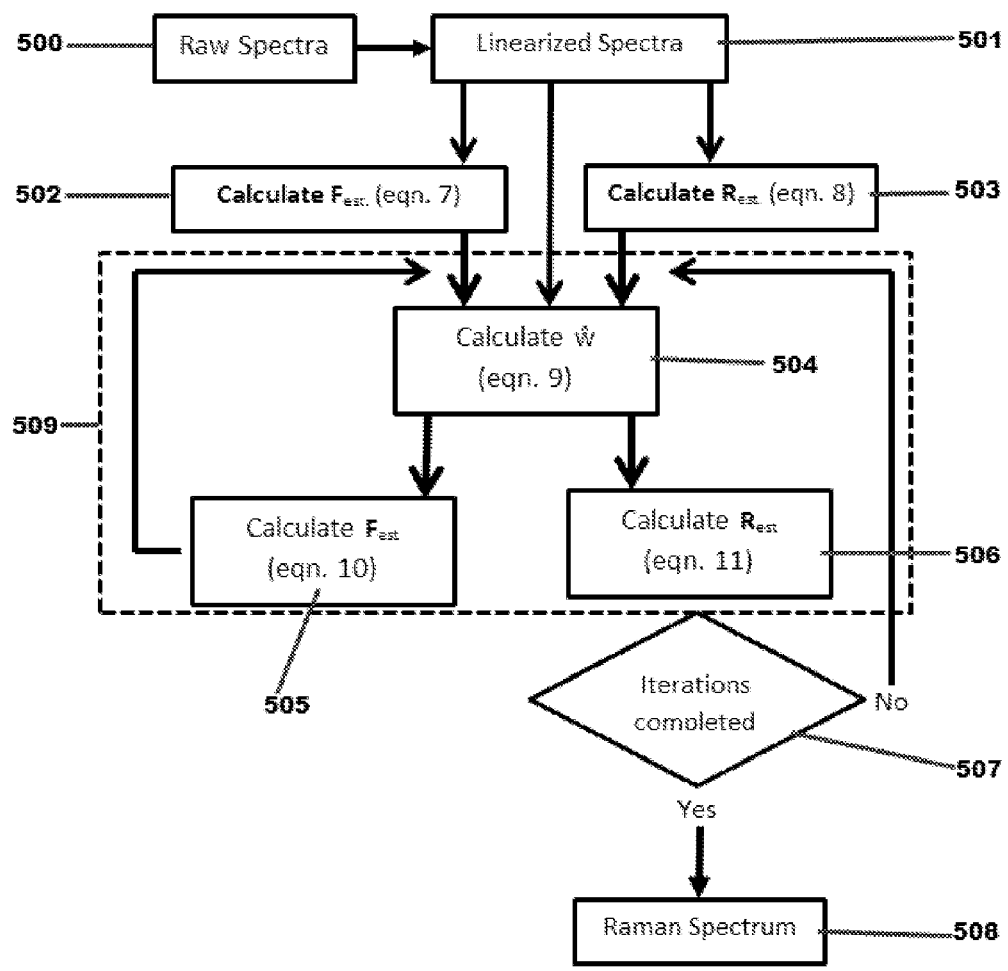

FIG. 13. This figure shows a method of processing shifted excitation Raman spectra to obtain a background-free Raman spectrum.

Figure 14:
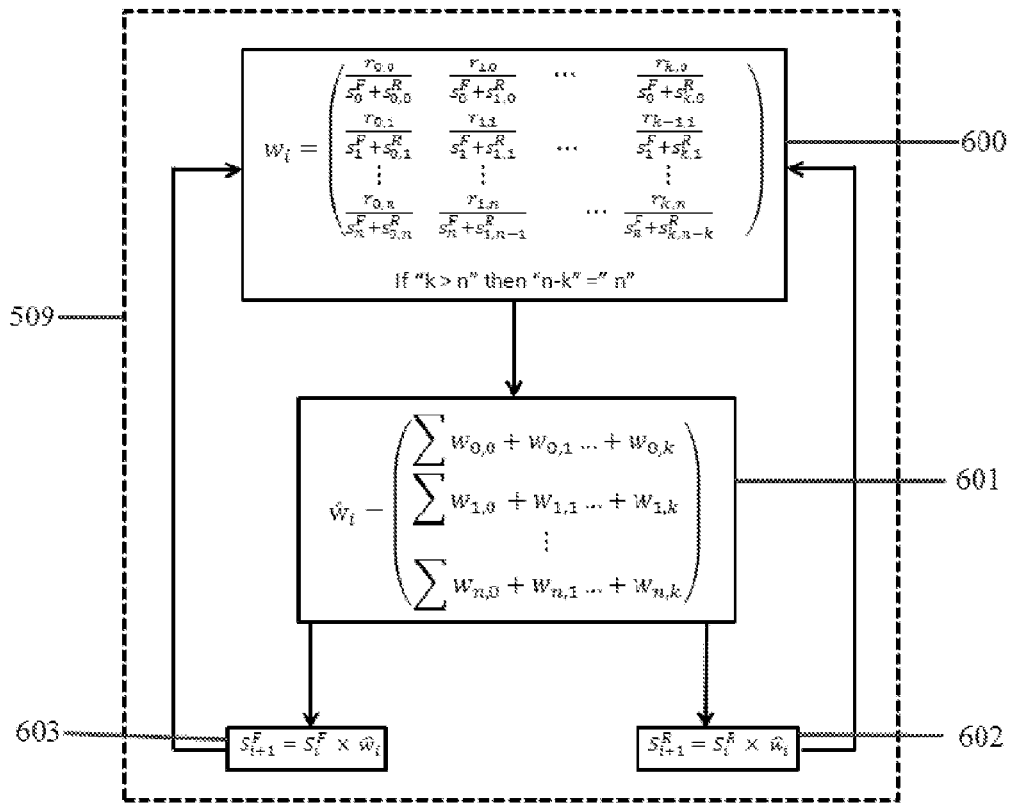

FIG. 14. This figure shows an embodiment of the data processing 509 (FIG. 13).

Figure 15:
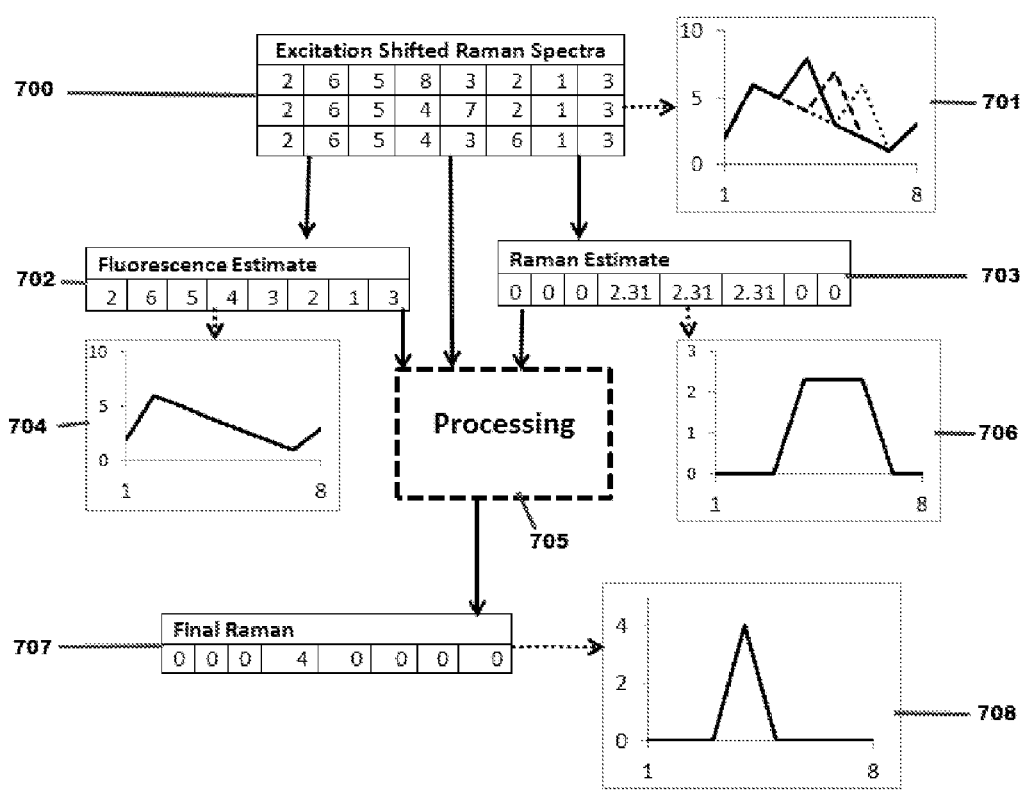

FIG. 15. This figure shows a numerical and graphical example of extracting a back-ground free Raman spectrum from shifted excitation Raman spectra with graphical depictions of initial, intermediate, and final values.

Figure 16:
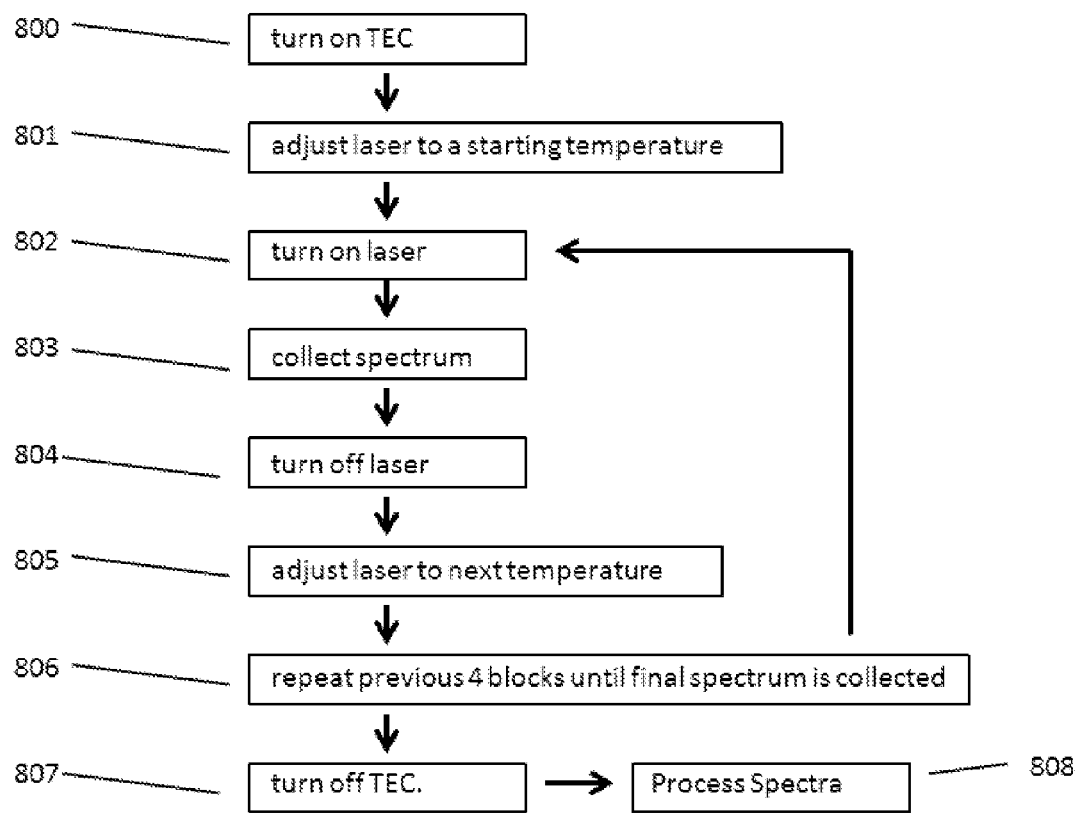

FIG. 16. This figure shows a flow diagram of operation.

DETAILED DESCRIPTION

FIGS. 1-5 and FIG. 13

First Embodiment

In one embodiment of the present invention a Raman spectrometer such as that shown in FIG. 1 is used. In this embodiment, a thermo-electric cooled distributed-Bragg-reflector (DBR) diode laser (100) which emits single mode radiation centered substantially at 785 nm is used as the excitation source. Detail of 100 is given in FIGS. 2 and 3. The emitted radiation is collimated using an asphere collimating lens (101). The emitted radiation is filtered using a laser band-pass filter (103). The band-pass filter (103) is designed such that it substantially passes laser radiation with a 5 nm wide FWHM pass band while not substantially passing radiation outside of the pass band. The filtered and collimated radiation is reflected by a dichroic beamsplitter (104) towards an asphere focusing lens (102) which is used to focus the radiation onto a sample. The dichroic beamsplitter is designed such that it substantially reflects light which can substantially pass through 103, and substantially passes light which is of greater wavelength than the reflected light. Irradiation of the sample results in the generation of Raman scattering (excitation) from the sample which is characteristic of the sample. The asphere lens 102 is also used to collimate the Raman signal originating from the irradiated sample. The resulting collimated signal may contain additional components other than Raman such as fluorescence. This collimated signal is passed through the beamsplitter (104) and is filtered by a long pass filter (105) and focused using a doublet achromat lens (106) onto a rectangular slit (107) which is 50 microns in width and 3 millimeters in height. The long pass filter (105) is designed such that it does not pass substantially the laser radiation while passing substantially the Raman signal. A doublet achromat collimating lens (108) is used to collimate the signal passing through the slit (107). The collimated signal is filtered by a long pass filter (109) which is substantially similar to 105 and dispersed using a volume holographic transmission grating (110). The dispersed signal is focused using a doublet achromat lens (111) onto a silicon CCD detector (112). The components 107, 108, 109, 110, 111, and 112 are enclosed so that the slit (107) is substantially the only entrance for light. The components 101, 102, 103, 104, 105, 106, 107, 108, 109, 110, 111, and 112 are enclosed so that substantially the only entrance for light is 101 and 102. The detector 112 is connected to an electronic CCD controller board 113 which allows collection of the detected analog signal, and conversion of the analog signal into a digital format. An electronic board 114 contains a constant current diode laser driver and a thermoelectric controller for powering the laser and controlling its temperature. A central processing unit (CPU) on 113 is used to control 114. The CPU on 113 is used to communicate with a computer which can carry out processing of the digital signals and allow for a human interface. The CPU on 113 is used to synchronize the collection of the spectra with the setting of the diode laser temperature and the turning on and turning off of the diode laser.

When a light irradiates a sample, an optical signal can be generated which is often composed of both a Raman component and a fluorescence component. A laser can be used to generate the light which is used to irradiate the sample. The laser can be referred to as the excitation source. In this embodiment, Raman spectra of a sample can be generated using several different excitation wavelengths by varying the temperature of the DBR laser. An example of Raman spectra generated using this configuration is given in FIG. 4. A schematic of the DBR laser 300 is shown in FIG. 2A. The DBR laser emits single-mode 785 nm radiation at 25° C. The Bragg grating of the DBR laser is a periodic structure etched into the GaAs substrate at the rear facet of the diode cavity 299 (FIG. 2D). Emission of radiation from the laser occurs at the front facet of the diode cavity 297 (FIG. 2A). Hence the laser and the Bragg grating consist of a contiguous and monolithic structure 300 on the same substrate. This facilitates the grating and the laser temperature being maintained in unison at a set temperature. FIG. 3A shows the temperature controlled DBR laser 100 as comprising the DBR laser 300 mounted to an aluminum nitride submount 301 along with a thermistor 302. The sub-mount 301 is mounted onto a heat-sink 303 which is mounted onto a Peltier thermoelectric cooler 304 (TEC). The opposing side of the TEC 304 is mounted onto the base of a T08 electronic package 305. The package 305 provides pins for electrical connections from 114 to the laser 300 and the thermistor 302. The thermistor allows the temperature of the diode laser to be monitored and controlled via 113 and 114. For the laser used to generate the data in FIG. 4, the temperature of the laser 300 is changed to a set-point value; where the emitting wavelength of the laser at a given temperature is equal to:

$$\lambda = 785 \text{ nm} + \left(0.074 \, \frac{\text{nm}}{\text{°C.}} \times \Delta T\right) \quad (4)$$

and where $\Delta T$ is the set-point temperature of the TEC minus 25° C. The feedback from the Bragg grating stabilizes the modal structure of the laser so that when the laser is operated at a constant current, a range of $\Delta T$ exceeding 15° C. is obtainable without a change in the single-mode modal structure of the laser output (i.e., no mode hops occur). Once a desired optical output is chosen, its value can be varied typically by less than 15% to obtain a current which provides a mode-hop free range over a very large temperature change of the laser. This is an unexpected result since it is well known by those experienced in the art of Raman spectroscopy that large changes in laser temperature cause diode lasers to mode hop. In a more general form, equation 4 can be re-written for any type of Bragg grating stabilized diode laser as:

$$\lambda = CW + (K \times \Delta T) \quad (5)$$

where CW is the center wavelength of the diode laser at a specific temperature, K is the change in laser wavelength per degree Celcius, and $\Delta T$ is the set-point temperature of the TEC minus the temperature where the laser has a wavelength equal to CW.

In this embodiment, a sample-incident optical power output of 50 mW is selected and the laser is run in constant current mode (100 mA) by using a fixed resistance on the thermoelectric controller (TEC) board 114. The TEC controller board 114 is capable of 0.01° C. precision. In the present embodiment, this provides a stable mode-hop free temperature range from 16-34° C. A typical measurement consists of collecting Raman spectra at DBR laser temperatures of 20, 23, 26, and 29° C. (i.e., four sequential excitations). This yields excitation wavelengths of 784.630, 784.852, 785.074, and 785.296 nm, respectively and gives a constant excitation shift of 0.222 nm. When converted to wavenumbers ($cm^{-1}$), this gives a separation of substantially 3.60 $cm^{-1}$ between the different excitations. The $cm^{-1}$ scale is linear to 0.01 $cm^{-1}$ over such a small change in wavelength. We have not been able to observe any changes in laser quality resulting from back-reflections into the diode cavity resulting from sample placement even as the laser temperature is changed. This is an unexpected result since both changes to temperature and back-reflections are known to cause diode lasers to mode hop. For this reason an optical isolator in front of the diode laser was omitted in the current embodiment, but this does not preclude its use in another embodiment.

Once the shifted excitation Raman spectra are acquired (FIG. 4), the Raman spectrum can be extracted using data processing as described subsequently. An example of a resulting background free Raman spectrum (produced by processing the data in FIG. 4) is given in FIG. 5B. In addition, an FT-Raman spectrum is shown in FIG. 5A for comparison. Since neither of the spectra are corrected for spectral intensity throughput, the relative intensities of the peaks are not identical. This is particularly true when comparing the fingerprint region (below 2500 $cm^{-1}$ on the x-scale) to the CH-stretching region (above 2500 $cm^{-1}$ on the x-scale). For the dispersive instrument, the silicon CCD detector has a minimum quantum efficiency for the CH-stretching spectral range (wavelengths greater than 1020 nm), while for the FT-Raman spectrum, this range corresponds to the maximum quantum efficiency of the InGaAs detector used. As shown, the elimination of the background in FIG. 5B is a significant advantage of the present embodiment. The total acquisition time of the spectrum using this embodiment of the present invention is less than 5 seconds while that of the FT-Raman is 120 seconds. In addition, the laser power for the present embodiment is 50 mW while that for the FT-Raman is 800 mW. These two facts and the high quality of the spectrum shown in FIG. 5B demonstrate the significant advantage of the present embodiment of the invention. In addition, as shown in FIG. 1, the very small size of the present embodiment is a significant advantage. The small size of the embodiment allows for handheld use and portability. Remarkably, FIGS. 1-5 demonstrate that the present embodiment can provide Raman data which is of a quality of an FT-Raman spectrometer but requiring a fraction of the time, a fraction of the laser power, a fraction of the instrument size, and a fraction of the instrument cost.

The data processing of the shifted excitation Raman spectra is described below and in FIG. 13. The Raman spectra are calibrated to an axis which is linear in energy, e.g. wavenumber units, where the separation between the spectral positions is substantially the same as the wavenumber separation between the laser excitations used to acquire each of the Raman spectra. The Raman spectra can be described using a matrix, R:

$$R = \begin{pmatrix} r_{0,0} & \cdots & r_{0,n} \\ \vdots & \ddots & \vdots \\ r_{k,0} & \cdots & r_{k,n} \end{pmatrix} \tag{6}$$

where the number of rows is equal to the number of excitations (K) and the number of columns is equal to the number of spectral positions (N). Each element of the matrix has two unique indices k and n, and is represented by $r_{k,n}$, where the maximum value for k is K−1, and the maximum value for n is N−1. An initial estimate of the background signal (e.g. fluorescence or any non-Raman signal) is obtained by taking the minimum of each column in matrix R:

$$S_0^F = (\min_k r_{k,0}, \min_k r_{k,1}, \ldots \min_k r_{k,N-1}) \tag{7}$$

where $S_0^F$ represents the vector containing the initial fluorescence estimate (e.g. the estimate at the $0^{th}$ iteration). An initial estimate of the Raman spectrum is obtained by calculating the standard deviation of each column in R:

$$S_0^R = \langle \sigma(r_{0,0}, r_{1,0}, \ldots r_{K-1,0}), \sigma(r_{0,1}, r_{1,1}, \ldots r_{K-1,1}), \ldots \sigma(r_{0,N-1}, r_{1,N-1}, \ldots r_{K-1,N-1}) \rangle \tag{8}$$

where the $r_{k,n}$ elements in parentheses indicate a particular column of matrix R and σ is the standard deviation of that column, and $S_0^R$ represents the vector containing the initial Raman estimate (e.g. the estimate at the $0^{th}$ iteration). Given these two vectors, an iterative approach can be used to solve for the pure Raman spectrum. This is done by calculating a weighting vector, $\hat{w}_i$, which is calculated with each iteration, i:

$$\hat{w}_i = \sum_{k=0}^{K-1} R_{k,n} \div (S_{i,n}^F + S_{i,n-k}^R) \tag{9}$$

where the division and addition operators are carried out element-wise. Then for each iteration, i, the fluorescence spectrum is calculated as:

$$S_{i+1}^F = S_i^F \times \hat{w}_i \tag{10}$$

and the Raman spectrum is calculated as:

$$S_{i+1}^R = S_i^R \times \hat{w}_i \tag{11}$$

For each subsequent iteration, the results of equations 10-11 are fed back into equation 9 and i is incremented by one. This iterative process is repeated until the desired Raman spectrum is obtained. Significantly, the number of calculations using this approach is proportional to k×N per iteration, while that of previous iteration methods is proportional to k×$N^2$ per iteration. For a spectral acquisition with 1000 spectral points (typical for dispersive Raman), this results in a decrease by 3 orders of magnitude in the number of calculations, resulting in total processing times of a fraction of a second using a conventional desktop computer. In addition, the simple nature of Eqn. 9-11 allows implementation with only a few lines of simple code in common computer languages such as C. In addition, since this embodiment does not require the inclusion or manipulation of a KN×2N shift matrix, there is a massive reduction in memory requirements for the CPU used to carry out the processing. A schematic of this aspect of the embodiment is shown in FIG. 13. It is recognized by readers experienced in the art of mathematics that in the embodiments incorporated in this disclosure, the index values in the equations cannot have negative values and that boundary conditions must be applied. An example of a boundary condition would be to set n−k in equation 9 to zero if it becomes negative.

Operation—FIG. 16

An operation of this embodiment is shown using a flow diagram in FIG. 16. The thermoelectric cooler is turned on 800 and the laser 300 is adjusted to a starting temperature 801. The laser is then turned on 802. The first Raman spectrum of the sample is collected 803. The laser is turned off 804. The laser is adjusted to the next temperature using the thermoelectric cooler 805. The laser is then turned on again 802 and the second Raman spectrum is collected at the shifted excitation which results from the new temperature being applied 805. Steps 802-805 are repeated 806 until the total number of Raman spectra is equal to or exceeds 3. Following this procedure, all of the Raman spectra will have been acquired at excitations which are shifted in wavelength with respect to each other. The TEC is then turned off 807 and the Raman spectra are processed to give the final Raman spectrum 808. As demonstrated by the flow diagram in FIG. 16, it is necessary to carry out the acquisition of the spectra after the temperature of the diode laser is changed, thus a way to synchronize the spectral acquisition with the temperature controller is required. In this embodiment, the synchronization is accomplished using a programmed microcontroller. In other embodiments this can be accomplished using human interaction with the device or by using more advanced computers with or without human interaction, or by using a combination of controllers and/or computers either with or without human interaction.

FIGS. 6-12 and FIGS. 14-15

Examples of Additional Embodiments

Example 1

PCA Extraction

The Raman spectra acquired at each unique laser excitation can be described by a matrix R as shown in equation 6. Using conventional matrix decomposition such as singular value decomposition (SVD), R can be related to a loadings matrix L:

$$R = TL^T \quad (12)$$

where $L^T$ is the transpose of the loadings matrix and where there are K rows in L and each row corresponds to a principal component (loading vector) which describes orthogonal variance in R. The scores matrix T relates how much of each principal component is required to reconstruct each spectrum in R. A characteristic of the loading matrix is that the principal components are sorted in descending order of variance. Since the principal variation of R is the change in excitation lasers when collecting the data, and since this principally only affects the Raman signal, the first principal component describes the variation in the Raman signal as the excitation lasers are changed and is observed as a pseudo-derivative Raman spectrum. The spectral components which are independent of small changes in excitation wavelength (e.g., fluorescence) as well as a portion of the random noise are described by the higher principal components. This method is similar to SERDS in terms of generating a spectrum which has a derivative shape, but has the added advantage of reducing spectral noise as opposed to increasing it. In this embodiment of the current invention, PCA is used to extract the Raman data from shifted excitation spectra acquired using a Raman spectrometer comprising a temperature controlled diode laser with Bragg grating feedback. An example is given in FIGS. 9F and 10F.

Example 2

Extraction Using a Shift-Matrix

In this embodiment a Raman spectrum is extracted from shifted excitation Raman spectra acquired using a Raman spectrometer comprising a temperature controlled diode laser with Bragg grating feedback by relating the desired outcome (separated Raman spectrum and fluorescence spectrum) to the collected data (R) using an operator matrix H:

$$HS = R \quad (13)$$

where S is a 1×2N matrix containing a column vector of spectral events which are independent of small changes in excitation wavelength such as fluorescence ($S^F$) and a column vector corresponding to the true Raman signal ($S^R$):

$$S = \begin{pmatrix} S^F \\ S^R \end{pmatrix} = \begin{pmatrix} \begin{pmatrix} S_0^F \\ \vdots \\ S_n^F \end{pmatrix} \\ \begin{pmatrix} S_0^R \\ \vdots \\ S_n^R \end{pmatrix} \end{pmatrix} \quad (14)$$

where both the fluorescent spectrum ($S^F$) and the Raman spectrum ($S^R$) consists of N spectral positions. The spectral data matrix (R) is rewritten as a concatenated column vector of spectra:

$$R = \begin{pmatrix} R_0 \\ \vdots \\ R_k \end{pmatrix} = \begin{pmatrix} \begin{pmatrix} r_{0,0} \\ \vdots \\ r_{0,n} \end{pmatrix} \\ \vdots \\ \begin{pmatrix} r_{k,0} \\ \vdots \\ r_{k,n} \end{pmatrix} \end{pmatrix} \quad (15)$$

where each spectrum has N spectral positions of intensity $r_{k,n}$ at each spectral position, and there are a total number of spectra corresponding to the number of excitations (K). The operator matrix H consists of two columns of N×N square sub-matrices:

$$H = \begin{pmatrix} H_0^F & H_0^R \\ H_1^F & H_1^R \\ H_2^F & H_2^R \\ \vdots & \vdots \\ H_k^F & H_k^R \end{pmatrix} \quad (16)$$

where the first column corresponds to sub-matrices which describe the spectral position of fluorescence intensity ($H_k^F$) at each excitation (k), and the second column corresponds to sub-matrices which describe the spectral position of Raman intensity at each excitation ($H_k^R$). An iterative approximation algorithm is used with a reasonable initial estimate of $S^R$ and $S^F$ (where $S^F$ can be regarded as any non-Raman signal). For example, selecting the maximum spectral intensity from each k spectrum at each spectral position n will yield an initial Raman estimate ($S_0^R$). Likewise, selecting the minimum spectral intensity from each k spectrum at each spectral position n will minimize Raman contributions yielding an initial fluorescence estimate ($S_0^F$). Alternatively, equation 8 can be used to provide an initial Raman estimate. An example of an equation using this iterative approach incorporating an operator matrix is shown in eqn. 17:

$$S_{i+1} = S_i \times (H^T (R \div HS_i)) \quad (17)$$

where multiplication and division operators are carried out element-wise and i is the iteration number (H, S, and R remain defined as in the previous three equations).

Example 3

Modifications to Processing Aspect

In the first described embodiment of the present invention, equations 5-11 and FIG. 13 are used to describe how to extract the Raman data from the shifted excitation spectra. A part of the simplicity of this aspect of the first embodiment results from the use of a fixed change in wavelength (excitation shift) between the utilized excitations. In equation 9, the index k=0 refers to the excitation at the lowest wavelength, and the index k=K−1 refers to the excitation at the greatest wavelength. Each increase in the k index corresponds to an increase in excitation wavelength. It is recognized by users experienced in the art of mathematics that in another embodiment of the present invention the order of excitations in terms of the wavelength can be reversed and the Raman data still extracted. For example, the following equation can be used in this embodiment:

$$\hat{w}_i = \sum_{k=K-1}^{0} R_{k,n} \div (S_{i,n}^F + S_{i,n+k}^R) \quad (18)$$

It is recognized by users experienced in the art of Raman spectroscopy that in another embodiment of the present invention, the shifted excitation Raman spectra can be acquired in any order and then sorted in ascending or descending order of excitation wavelength before processing the data. It should also be recognized by readers experienced in the art of mathematics that the value of n+k in equation 18 is bounded by N−1.

In another embodiment of the present invention, the spacing between the excitation wavelengths is not constant in energy units (e.g., wavenumbers). In this embodiment, a vector containing the shift in spectral positions for each excitation is used. As an example, an equation can be written as:

$$\hat{w}_i = \sum_{k=0}^{K-1} R_{k,n} \div \left(S_{i,n}^F + S_{i,n-j_k}^R\right) \quad (19)$$

where $j_k$ is an element of vector j, and vector j contains the shift in spectral positions for each excitation. For example, if all of the excitation shifts are substantially the same in terms of the spectral positions, then for K excitations j would be equal to:

$$j=(0, 1, \ldots K-1) \quad (20)$$

As another example, for 3 excitations (K=3), where the second excitation is three spectral units greater than the first excitation, and the third excitation is one spectral unit greater than the second excitation, then j would be equal to:

$$j=(0, 3, 2) \quad (21)$$

One experienced in the art of mathematics will realize that these additional embodiments of equations 9-11, offer the flexibility to vary the number of, the value of, and the order of the excitations.

Use of equations 9-11 or use of equations 13-17 to extract a Raman spectrum require that the spectra consist of uniformly spaced points which are proportional to energy (eg. wavenumbers). Methods to accomplish this requirement are well known and involve calibrating the spectra to an axis which is proportional to energy (e.g. wavenumbers). An additional requirement is that the differences in energy units between the various excitations (eg. wavenumber difference) corresponds to the difference between consecutive spectral data points of the spectra or corresponds to an integral multiple of the difference between consecutive spectral data points of the spectra. This requirement is accomplished using embodiments of the present invention by selecting the appropriate laser temperatures to obtain the desired excitation shifts. This is a significant advantage of the embodiments of the present invention. For prior art which relies on the use of a series of different lasers to provide different excitations, it is not possible to accomplish this without great expense (either monetarily or computationally) since all lasers used must be manufactured to be integral values of the spectral spacing or the spectral data must be interpolated to a very small spacing so that each excitation shift can be represented by an integral number of spacings (difference in energy of consecutive spectral points).

Example 4

Alternative Form of 509 and Numerical Example

Since equation 9 in the description of the first embodiment is based on element-wise math operations, it is instructive to the reader to display the element-wise operations in detail in another embodiment of this aspect. This is shown in FIG. 14. As shown, the element-wise operations are indicated in matrix 600 for shifted excitation Raman spectra consisting of N spectral positions and K excitations. As a further example, In FIG. 15 a numerical example is given where the values at each spectral position for three shifted excitation spectra are given 700 and the spectra are graphed 701. The numerical values corresponding to the calculated initial fluorescence estimate 702 using equation 7 and initial Raman estimate 703 calculated using equation 8 are given also and are plotted, 704 and 706, respectively. The numerical values for the final Raman spectrum 707 are given and graphed 708. The processing 705 required to produce 707-708 corresponds to 100 iterations of 509.

Example 5

Analysis of Catechol

Another example of an embodiment is provided in FIG. 6 with the spectra of catechol. FIG. 6a corresponds to the FT-Raman spectrum of catechol (120 s acquisition and 800 mW); FIG. 6b corresponds to the unprocessed dispersive Raman spectrum at 20° C. (2.5 s acquisition and 50 mW), and FIG. 6c corresponds to the processed sequentially shifted excitation spectra (SSE) acquired at three laser temperatures (2.5 s×3 acquisitions and 50 mW). For the dispersive Raman of the catechol sample, the fluorescence spectrum has a significantly different shape than the spectrum of the dimethyl glyoxime; but the embodiment yields results that are comparable to the FT-Raman. Although it should be noted, that for the FT-Raman spectrum some fluorescence background is still present.

Example 6

Removing Room Lights and Non-sample Fluorescence

Another comparison is given in FIG. 7 for the spectra of magnesium carbonate. In this embodiment, due to the simplicity of the carbonate ion and its high symmetry, only a single Raman vibration is expected near 1180 cm$^{-1}$. The high electronegativity of the oxygen atoms in the carbonate ion result in a large degree of polarization of the binding electrons which results in a very low Raman cross-section for the ion (i.e., small change in polarizability). This results in weak scattering and thus lower S/N for both the FT-Raman (FIG. 7a) and the Raman spectrum extracted from shifted excitation Raman spectra (FIG. 7c). For the raw dispersive spectrum (FIG. 7b) the dominant spectral features are due to the fluorescence of the borosilicate NMR tube that holds the sample and weak emission lines due to the room lights. Since no effort was made to exclude room lights from this measurement, they were observed in the Dispersive Raman spectra when weak signals were present. The Raman spectrum of the process shifted excitation spectra (SSE) shows the elimination of interference from both the sample holder fluorescence and from the room lights.

Example 7

Removal of Sharp Fluorescence Peaks

A more complex sample is given in FIG. 8 for the Raman spectra of ceric ammonium sulfate. FIG. 8A corresponds to the FT-Raman spectrum (120 s and 800 mW); FIG. 8B corresponds to the unprocessed dispersive Raman spectrum at 20° C. (4 s and 50 mW), and FIG. 8C corresponds to the Raman spectrum extracted from sequentially shifted excitation Raman spectra (referred to as the SSE Raman spectrum) acquired at five laser temperatures (4 s×5 acquisition and 50 mW). For FIG. 8B, the 785 nm dispersive spectrum consists almost solely of fluorescence. In addition, the fluorescence of the f-block lanthanide ion is structured with peaks which have bandwidths which approximate that expected for Raman peaks for both the FT-Raman and dispersive Raman instruments. The inset in FIG. 8B magnifies the lower part of the fingerprint region by a factor of 25 so that the Raman peaks can be observed. Although background effects are still present, a one to one correspondence of these peaks with those in FIG. 8C can be observed (SSE Raman spectrum). For the FT-Raman, there is some correspondence also; however, the region close to 200 $cm^{-1}$ is very intense and broad relative to both the raw and SSE spectra. In addition, the sulfate peak at ~1000 $cm^{-1}$ is much broader than expected for the FT-Raman spectrum (see inset for FIG. 8A) and must have a fluorescence contribution. As expected, the fluorescence of the cerium ion using 1064 nm excitation is much different than that using 785 nm. It follows that the broad peak at 1250 $cm^{-1}$ and weak spectral features near 1700 $cm^{-1}$ observed for the FT-Raman spectrum correspond to fluorescence also. This is further justified by their absence in FIG. 8C when using SSE Raman. Although typical broad fluorescence backgrounds are easily discerned by the eye, a significant advantage of shifted excitation embodiments of the present invention over FT-Raman is the additional ability to discern sharp fluorescent features which have bandwidths which approach that of the Raman spectrum. Also, the fluorescence from such samples cannot be treated with baseline removal techniques such as polynomial fitting or derivatives.

Example 8

Comparison to SERDS and FT-Raman

The inability of FT-Raman to eliminate all of the fluorescence for some samples is further exemplified in FIG. 9A for the spectrum of acenaphthylene (cyclopentanaphthalene). For the FT-Raman, there is a significant broad undulating background even with 1064 nm excitation due to the polycyclic aromatic nature of the molecule. For the unprocessed 785 nm dispersive Raman spectrum, the fluorescence is several orders of magnitude more intense than that of the Raman. Despite this intense fluorescence, the processed four-temperature sequentially shifted excitation (SSE) data effectively eliminates the fluorescence while providing comparable signal to noise when compared to the FT-Raman spectrum. The same observations can be made in FIG. 10 for the spectra of 4-bromo-N,N-dimethylaniline. For these spectra, the signal to noise of the SSE Raman spectrum is slightly less than that of the FT-Raman spectrum. This is due to the much lower laser power and integration time for the SSE measurement.

As a comparison, the SERDS method is also included in FIGS. 9E and 10E using the same shifted excitation spectra that were used for the SSE Raman spectra (FIGS. 9C and 10C). For the SERDS calculation, only two spectra are required, so the best results are displayed (this always corresponded to the largest shift between spectra, ie, 20 C and 29 C). For acenaphthylene (FIG. 9), all methods give comparable signal-to-noise, but the Raman extracted from sequentially shifted excitation Raman spectra using equations 9-11 (SSE Raman) in FIG. 9C results in the lowest background followed closely by the standard deviation (SD) spectrum. However, the embodiments incorporating the standard deviation spectrum are difficult to interpret due to the doubling of peaks arising from the nature of the calculation. Both the SERDs and the embodiments using the PCA extracted spectra result in similar yet higher levels of background. It is easier to observe the noise component in the dispersive spectra acquired for 4-bromo-N,N-dimethylaniline (FIG. 10). The higher S/N for the SSE Raman can easily be seen relative to SD, SERDs, and PCA. Regardless, the SERDs and PCA methods still suffer from the fact that the remaining background results in a baseline which makes it difficult to retrieve the true Raman spectrum from the processed spectral data without using additional algorithmic background filtering methods.

Example 9

Derivative of SSE Raman

Since Raman is often used as a method of spectral identification, the argument may be put forward that spectral data in the derivative space is sufficient. As a comparison, the derivatives of the Raman spectrum extracted from sequentially shifted excitation spectra (SSE spectrum) of tris(hydroxymethyl)aminoethane is compared to those of PCA in FIG. 11. As shown, the derivative of the SSE spectrum (FIG. 11B) results in a spectrum with a flat background and with a higher S/N. An additional advantage of SSE over the SERDS and the PCA embodiment lies in the fact that the SSE experiment can be carried out under a wide range of excitation conditions without impacting the resolution of the Raman spectrum result. For both SERDS and PCA methods, however, the bandwidth and peak position of the resulting derivative peaks is a function of the excitation spacing. This is demonstrated in FIG. 11 where two different excitation profiles are used. The first excitation profile consists of acquiring the spectra at 20, 23, and 26° C.; while the second excitation profile consists of acquiring spectra at 20, 26, and 32° C. The change in the excitations for the experiment results in a change in peak bandwidth for the PCA data but not for the SSE data. Although not shown, the effect is even more dramatic for SERDS.

Example 10

Number of Iterations

An example of intermediate outputs during the application of the iterative processing algorithms as convergence is approached is given in FIG. 12. As shown for the spectra of dimethyl glyoxime, at least 1000 iterations are required before the final Raman spectrum is resolved. For samples with low levels of fluorescence or no fluorescence, this convergence is often reached with less iterations, while with samples with more dominating fluorescence, benefits may be realized by iterations approaching or exceeding 3000.

Alternative Embodiments

Users experience in the art of Raman spectroscopy will realize that the present invention is not limited to the embodiments disclosed in FIG. 1 and its description. This embodiment is provided to demonstrate the advantage of embodiments of the current invention and the advantage in providing a handheld article of manufacture. Additional embodiments can realize a handheld article of manufacture by replacing, eliminating, or adding to existing elements comprising embodiments of the current invention. For example, the holographic transmission grating can be replaced by one having more or less grooves per millimeter; the aspheres can be replaced by gradient refractive index lenses, spherical optics, diffractive optics, or by multi-element lenses; the doublets can be replaced by triplets, single element spherical optics, diffractive optics, gradient refractive index lenses, or by multi-element lenses; the slit can be replaced by a circular aperture or aperture of different geometry; filters may be eliminated or additional filters may be added or filters may be replaced with filters of different performance; the laser can be replaced with a laser of a different center wavelength; the CCD can be replaced with an array detector; the sizes of the elements can be changed to provide a larger or smaller embodiment; the focal lengths of the lenses may be adjusted to accommodate a different size of the embodiment or to realize additional advantages.

Users experience in the art of Raman spectroscopy will realize that additional embodiments of the present invention will also have advantages. Examples include a Raman spectrometer comprising a temperature controlled diode laser comprising a Bragg grating where said Raman spectrometer is used to collect Raman spectra at multiple excitations and said spectra are processed according to embodiments of the present invention to produce a substantially back-ground free Raman spectrum where said Raman spectrometer comprises at least one of a microscope, a spectrograph comprising mirrors, a spectrograph comprising lenses, a spectrograph comprising a combination of mirrors and lenses, a scanning monochromator, an FT-Raman spectrometer, a bench-top Raman spectrometer, an AOTF, a Raman spectrometer means. Examples of said Raman spectrometer means are described in the listed prior art references which are incorporated in this disclosure in their entirety.

Embodiments of the present invention can be operated in a variety of manners, in order to realize certain advantages such as minimizing electrical power consumption. One such embodiment of operation is shown in FIG. 16. Additional embodiments which may realize other or additional benefits include but are not limited to only turning the laser on once; only turning off the laser once; turning the laser on at any time prior to acquiring the spectrum; turning the laser off at any time after the spectrum has been acquired. Additional embodiments of the present invention are not limited to these examples. These examples are provided as an illustration of possible ways to operate embodiments of the present invention.

Aspects of embodiments of the present invention require the calculation of an initial Raman estimate and an initial fluorescence estimate to seed iterative algorithms. Although examples of ways to calculate these estimates have been given, additional embodiments of the present invention are not limited to these aspects. These examples are provided as an illustration of possible ways to determine these estimates.

Aspects of embodiments of the present invention have been described using equations. Although numerous examples have been given for the embodiments of these equations, users experienced in the art of mathematics will realize additional embodiments of the present invention by expressions through the use of computer code; mathematical alteration; and other means.

Readers experienced in the art of Raman spectroscopy and mathematics will realize that the intensities of raw Raman spectra are often transformed or normalized to realize certain advantages. Additional embodiments of the present invention can be realized by transforming or normalizing the shifted excitation Raman spectra before, during, or after data processing (e.g., 705 and 509) occurs. For example, in one embodiment of the present invention, the intensities of the raw Raman spectra 500 are normalized using a standard normal variate algorithm (SNV) which involves subtracting the mean of a spectrum from each of its intensities and then dividing the each intensity by the standard deviation of the spectrum. This embodiment has the advantage of correcting for variations in the optical power of the different excitations used to acquire the shifted excitation spectra. In another example, the spectra may be filtered by wavelet de-noising. Additional embodiments are not limited to these examples which are provided as an illustration of additional embodiments.

Although embodiments of the present invention have included the use of a DBR laser to generate shifted excitation spectra, the present invention should not be construed as limited to this type of laser, but this example is intended to provide illustration of embodiments which encompass any temperature controlled diode laser with optical feedback provided by a Bragg grating. An example is an embodiment of the present invention where a distributed feedback Bragg (DFB) diode laser comprising a TEC is used. A DFB diode laser is similar to a DBR laser as it consists of a monolithic structure comprising both the laser cavity and the Bragg grating and it can be mounted onto a TEC. Another example is an embodiment of the present invention where a diode laser is mounted on a TEC and a Bragg grating is mounted in a fixed position in front of the emitting cavity. In another example, equation 5 is used in an embodiment to determine the wavelength of a temperature controlled diode laser which has optical feedback from a fixed position Bragg grating. These examples should not be interpreted as limitations of embodiments of the present invention, but rather as illustrations of additional embodiments.

Although embodiments of the present invention have included the use of a diode laser excitation source with a center wavelength of 785 nm, users experienced in the art of Raman spectroscopy will realize additional embodiments of the present invention using alternative center wavelengths. Examples include, but are not limited to: 800 nm, 830 nm, 852 nm, 980 nm, 630 nm, and 635 nm. As an additional example, the center wavelength of the excitation source may encompass any value between 200 nm and 1100 nm.

CONCLUSIONS, RAMIFICATIONS, AND SCOPE

Accordingly, the reader will see that embodiments of the present invention can be used to generate background-free Raman spectra of samples rapidly and of high quality. In addition, embodiments for generating the back-ground free Raman spectra include a device which is small enough to be held in one hand and which uses a low laser power and can be operated in a mode which requires very low electrical power and allows for battery operation. Furthermore, an embodiment comprising the combination of a Raman spectrometer and an iterative processing algorithm (where the Raman spectrometer uses a temperature controlled diode laser comprising Bragg grating optical feedback) has the additional advantages in that:

- it is universally applicable to all molecular samples
- it offers superior signal to noise over existing methods and devices
- it is inexpensive to manufacture relative to existing devices
- it does not involve complex instrumentation
- it generates true Raman spectra not derivatives or differences
- it allows multiple articles of manufacture to operate using the same processing algorithm without having to adjust the algorithm or algorithm parameters
- it is computationally orders of magnitude more efficient than existing methods using iterative algorithms
- it removes fluorescence backgrounds which are orders of magnitude larger than the Raman signal
- it removes room lights and fluorescence signals from sample containers or impurities
- it provides a higher signal to noise Raman spectrum than ordinary dispersive Raman even when a background is not present
- it allows multiple articles of manufacture to provide the same excitation wavelengths
- it allows multiple articles of manufacture to provide the same excitation shifts
- it allows an article of manufacture to provide identical shifts in excitation
- it allows for an article of manufacture which can adjust excitation wavelengths, excitation shifts, and the number of excitations in a rapid manner with no change to the article of manufacture and at user discretion.

Although the description above contains many specificities, these should not be construed as limiting the scope of the embodiments but as merely providing illustration of some of several embodiments. Thus the scope of the embodiments should be determined by the appended claims and their legal equivalents, rather than by the examples and specificities given.

We claim:

1. A device comprising:
   a. a diode laser excitation means for irradiating a sample and generating an optical signal comprising a plurality of Raman wavelengths,
   b. a Bragg grating means for providing optical feedback to said diode laser excitation means,
   c. a temperature controller means for setting the temperature of said diode laser excitation means to a predetermined plurality of temperatures in a serial manner wherein said plurality of predetermined temperatures comprises at least a first temperature, a second temperature, and a third temperature,
   d. a dispersive spectrometer means for acquiring said optical signal where said dispersive spectrometer means comprises an optical dispersion means for dispersing said plurality of Raman wavelengths into a plurality of spatially resolved Raman wavelengths and said dispersive spectrometer means comprises a multi-element detector for simultaneously detecting said plurality of spatially resolved Raman wavelengths,
   e. a synchronization means for synchronizing said dispersive spectrometer means and said temperature controller means.

2. The device of claim 1 wherein a distributed Bragg reflector laser comprises said diode laser excitation means and said Bragg grating means.

3. The device of claim 1 wherein a distributed feedback Bragg laser comprises said diode laser excitation means and said Bragg grating means.

4. The device of claim 1 wherein said Bragg grating means comprises a volume holographic grating.

5. The device of claim 1 wherein said optical dispersion means comprises a grating.

6. The device of claim 5 wherein said grating comprises a volume holographic transmission grating.

7. The device of claim 1 wherein said multi-element detector comprises a CMOS detector.

8. The device of claim 1 wherein said multi-element detector comprises a CCD detector.

9. The device of claim 1 wherein said dispersive spectrometer means comprises a plurality of lenses.

10. The device of claim 1 wherein said dispersive spectrometer means comprises a plurality of filters.

11. The device of claim 1 wherein said temperature controller means comprises a thermo-electric cooler.

12. The device of claim 1 wherein said synchronization means comprises a computing means.

13. The device of claim 1 wherein said plurality of temperatures comprises temperatures greater than 15 degrees Celsius and less than 35 degrees Celsius.

14. A method of generating a Raman spectrum which is substantially free of background interference comprising the steps of:
   a. providing a diode laser excitation means for irradiating a sample and generating an optical signal comprising a plurality of Raman wavelengths,
   b. providing a temperature controller means for setting the temperature of said diode laser excitation means,
   c. providing a dispersive spectrometer means for acquiring said optical signal where said dispersive spectrometer means comprises an optical dispersion means for dispersing said plurality of Raman wavelengths into a plurality of spatially resolved Raman wavelengths and said dispersive spectrometer means comprises a multi-element detector for simultaneously detecting said plurality of spatially resolved Raman wavelengths,
   d. providing a synchronization means for synchronizing said dispersive spectrometer means, said temperature controller means, and said diode laser excitation means,
   e. using said synchronization means to cause said temperature controller means to set the temperature of said diode laser excitation means to a plurality of temperatures comprising a number of predetermined temperatures where said number is greater than two,
   f. using said synchronization means to cause said diode laser excitation means to irradiate said sample when said diode laser excitation means is at said predetermined temperatures,
   g. acquiring a plurality of Raman spectra using said synchronization means to cause said dispersive spectrometer means to acquire at least one spectrum while said diode laser excitation means is at each of said predetermined temperatures and while said diode laser excitation means irradiates said sample,
   h. providing a computation means,
   i. processing said plurality of Raman spectra using said computational means to generate said Raman spectrum whereby said Raman spectrum is substantially lacking background-interference.

15. The method of claim 14 wherein said synchronization means comprises a processing means.

16. The method of claim 14 wherein said synchronization means comprises a human means.

17. A method of generating a Raman spectrum which is substantially free of background interference comprising the steps of:
   a. providing a dispersive Raman spectrometer to acquire Raman spectra where said dispersive Raman spectrometer comprises an excitation source which can be adjusted to a predetermined excitation wavelength and used to generate a Raman spectrum from a sample,
   b. acquiring a group comprising at least three Raman spectra using said dispersive Raman spectrometer where each of the said Raman spectra is acquired at a substantially different excitation wavelength and where the difference in energy between any of said excitation wavelengths is substantially equal to a positive non-zero integer value times the smallest separation in energy of said excitation wavelengths,
   c. providing a computational means
   d. computing a Raman estimate means from said group using said computational means,
   e. computing a non-Raman estimate means from said group using said computational means,
   f. computing a Raman spectrum from said Raman estimate means, said non-Raman estimate means, and said group using said computational means and an algorithm means,
   whereby said Raman spectrum is generated substantially free of background interference.

18. The method of claim 17 wherein said positive non-zero integer value is equal to one.

19. The method of claim 17 wherein said dispersive Raman spectrometer comprises a volume holographic transmission grating.

20. The method of claim 17 wherein said algorithm means is an iterative algorithm.

21. The method of claim 20 wherein an iteration of said iterative algorithm produces a new Raman estimate and a new non-Raman estimate.

22. The method of claim 21 wherein said iteration is repeated more than ten times.

23. The method of claim 21 wherein said new Raman estimate is equal to the dot product of said Raman estimate and a weighting vector.

24. The method of claim 21 wherein said new non-Raman estimate is equal to the dot product of said non-Raman estimate and a weighting vector.

25. The method of claim 17 wherein said algorithm means comprises Principle Component Analysis PCA.

* * * * *